(12) United States Patent
Rousseau

(10) Patent No.: US 10,548,753 B2
(45) Date of Patent: Feb. 4, 2020

(54) PASSIVE CALORIC BYPASS DEVICE

(71) Applicant: Ethicon, Inc., Somerville, NJ (US)

(72) Inventor: Robert A. Rousseau, Ottsville, PA (US)

(73) Assignee: Ethicon, Inc., Somerville, NJ (US)

( * ) Notice: Subject to any disclaimer, the term of this patent is extended or adjusted under 35 U.S.C. 154(b) by 171 days.

(21) Appl. No.: 15/405,602

(22) Filed: Jan. 13, 2017

(65) Prior Publication Data

US 2018/0200094 A1 Jul. 19, 2018

(51) Int. Cl.
*A61F 5/00* (2006.01)

(52) U.S. Cl.
CPC .......... *A61F 5/0076* (2013.01); *A61F 5/0033* (2013.01)

(58) Field of Classification Search
CPC .... A61F 5/0033; A61F 5/0076; A61F 5/0036; A61F 5/0043
See application file for complete search history.

(56) References Cited

U.S. PATENT DOCUMENTS

| | | | |
|---|---|---|---|
| 4,134,405 A | 1/1979 | Smit | |
| 4,315,509 A | 2/1982 | Smit | |
| 4,398,910 A | 8/1983 | Blake et al. | |
| 4,501,264 A | 2/1985 | Rockey | |
| 4,641,653 A | 2/1987 | Rockey | |
| 5,306,300 A | 4/1994 | Berry | |
| 5,820,584 A | 10/1998 | Crabb | |
| 7,211,114 B2* | 5/2007 | Bessler | A61F 2/07 623/23.65 |
| 7,753,870 B2* | 7/2010 | Demarais | A61B 17/12099 604/8 |
| 7,794,447 B2 | 9/2010 | Dann et al. | |
| 8,814,898 B2 | 9/2014 | Gaur et al. | |
| 8,845,674 B2 | 9/2014 | Brister et al. | |
| 2003/0040804 A1* | 2/2003 | Stack | A61F 2/04 623/23.7 |
| 2003/0040808 A1 | 2/2003 | Stack et al. | |

(Continued)

FOREIGN PATENT DOCUMENTS

| WO | 2016/067087 A2 | 5/2016 |
|---|---|---|
| WO | 2016/088055 A1 | 6/2016 |

OTHER PUBLICATIONS

Trout, David L. et al. "Dietary Influences on Gastric Emptying of Carbohydrate versus Fat in the Rat". The Journal of Nutrition, vol. 107, (1977), pp. 104-111.

(Continued)

*Primary Examiner* — Leslie R Deak

(57) ABSTRACT

A novel medical device for treating obesity is disclosed. The device is inserted through the oral cavity and into the digestive tract of a human. The device is a passive catheter-style structure that preferentially directs a significant volume of the high calorie fluidic components of the chyme through the digestive tract, preventing exposure to the absorptive tissues of the digestive tract and, in some forms, stimulates negative feedback to the patient when simple sugars and carbohydrates are consumed. The device may be installed or removed though the use of standard endoscopy, or may be offered in the form of an ingestible device. The device may be inflatable or preformed for use within the digestive tract. Also disclosed is a novel method of using the medical device to control obesity.

9 Claims, 27 Drawing Sheets

(56) References Cited

U.S. PATENT DOCUMENTS

| | | |
|---|---|---|
| 2003/0093117 A1 | 5/2003 | Saadat |
| 2003/0120265 A1 | 6/2003 | Deem et al. |
| 2003/0144708 A1 | 7/2003 | Starkebaum |
| 2012/0095483 A1 | 4/2012 | Babkes et al. |
| 2013/0226219 A1* | 8/2013 | Brister .................. A61F 5/0089 606/192 |
| 2014/0275747 A1 | 9/2014 | Connor |

OTHER PUBLICATIONS

International Search Report dated May 4, 2018 for International Application No. PCT/IB2018/050106.

* cited by examiner

PASSIVE CALORIC BYPASS DEVICE

FIELD OF THE INVENTION

The field of art to which this invention pertains is medical devices useful in the treatment of obesity, more particularly removable medical devices that are implanted in the digestive tract of a human.

BACKGROUND OF THE INVENTION

According to studies reported by the Centers for Disease Control and Prevention (CDC): the National Health and Nutrition Examination Survey (NHANES) and the National Health Interview Survey (NHIS), more than two-thirds (68.8 percent) of adults over 20 years of age are considered to be overweight or obese. Additionally, more than one-third (35.7 percent) of adults are considered to be obese and more than 1 in 20 (6.3 percent) have extreme obesity.

Additionally, the National Institute of Health reports that overweight and obesity are risk factors for type 2 diabetes, heart disease, high blood pressure, and other health problems such as nonalcoholic fatty liver disease (excess fat and inflammation in the liver of people who drink little or no alcohol), osteoarthritis (a health problem causing pain, swelling, and stiffness in one or more joints), some types of cancer: breast, colon, endometrial (related to the uterine lining), and kidney as well as stroke.

Not exclusively a United States problem, worldwide obesity ranges are also increasing dramatically. The World Health organization reports that Worldwide obesity has more than doubled since 1980 and in 2014, more than 1.9 billion adults, 18 years and older, were overweight. Of these over 600 million were obese.

There is no single cause of all overweight and obesity and although the physiology and psychology of obesity are complex, the medical consensus is that the key contributing factor is an over intake of calories combined with reduced energy expenditures. There is no single approach that can help prevent or treat overweight and obesity. Treatment may include a mix of behavioral treatment, diet, exercise, and sometimes weight-loss drugs. In some cases of extreme obesity, weight-loss surgery may be an option.

Bariatrics is the field of medicine encompassing the study of overweight, its causes, prevention and treatment. Bariatric surgery is a treatment for morbid obesity that involves alteration of a patient's digestive tract to encourage weight loss and to help maintain normal body weight. Known bariatric surgery procedures include jejuno-ileal bypass, jejuno-colic shunt, biliopancreatic diversion, gastric bypass, Roux-en-Y gastric bypass, gastroplasty, gastric banding, vertical banded gastroplasty, and silastic ring gastroplasty.

There have been many attempts in the past to surgically modify patients' anatomies to attack the over-consumption problem by reducing the desire to eat. Stomach stapling, or gastroplasties, to reduce the volumetric size of the stomach, therein achieving faster satiety, were performed in the 1980's and early 1990's. Although patients were able to achieve early weight loss, sustained reduction was not obtained. The reasons are not all known, but are believed to be related to several factors. One of which is that the stomach stretches over time increasing volume while psychological drivers motivate patients to find creative approaches to literally eat around the smaller pouch.

There are two surgical procedures that successfully produce long-term weight loss; the Roux-en-Y gastric bypass and the biliopancreatic diversion with a duodenal switch (BPD). Both procedures reduce the size of the stomach plus shorten the effective-length of intestine available for nutrient absorption. Reduction of the stomach size reduces stomach capacity and the ability of the patient to take in food. Bypassing the Duodenum makes it more difficult to digest fats, high sugar and carbohydrate-rich foods. One objective of the surgery is to provide feedback to the patient by producing a dumping syndrome if they do eat these food products. Dumping occurs when carbohydrates directly enter the jejunum without being first conditioned in the Duodenum. The result is that a large quantity of fluid is discharged into the food from the intestinal lining. The total effect makes the patient feel light-headed and results in severe diarrhea. For reasons that have not been determined the procedure also has an immediate therapeutic effect on diabetes.

Although the physiology seems simple, the exact mechanism of action in these procedures is not understood. Negative feedback is provided from both regurgitation into the esophagus and dumping when large volumes of the wrong foods are eaten. Eventually, patients learn that in order to avoid both these issues they must be compliant with the dietary restrictions imposed by their modified anatomy. In the BPD procedure, large lengths ofjejunum are bypassed resulting in malabsorption and therefore, reduced caloric uptake. In fact, the stomach is not reduced in size as much in the BPD procedure so that the patient is able to consume sufficient quantities of food to compensate for the reduced absorption. This procedure is reserved for the most morbidly obese as there are several serious side effects of prolonged malabsorption.

Laparoscopic techniques have been applied to these surgeries in an attempt to improve the patient outcomes. While the laparoscopic techniques provide fewer surgical complications, they continue to expose these very ill patients to high operative risk in addition to requiring an enormous level of skill by the surgeon.

While surgery seems to be an effective answer, the current invasive procedures may often times not be acceptable with the aforementioned and additional potential complications of anastomotic stricture, gallstone formation, gastroesophageal reflux, bowel obstruction, nutritional deficiencies requiring dietary modification and supplementation for life, incisional hernias, diarrhea, abdominal bloating, and malodorous flatus/stool.

Additionally, the devices that have been proposed as alternatives to surgical approaches in the literature, as well as the surgical approaches, provide a general approach of malabsorption of all nutritional components of the ingested foods. Further, the most favorable surgical procedure functions by the elimination of contact of ingested food with the absorptive tissues of the Duodenum. The mechanism of the bypass, while not being fully understood, appears to limit the absorption of the carbohydrate and simple sugar components of the ingested food, as evidenced by the generally immediate reduction in the blood sugar levels of treated patients. Additionally, devices or newer surgical approaches that demonstrate this reduction of blood sugars are deemed successful, despite the potential creation of generalized malnutrition.

In the article "Dietary Influences on Gastric Emptying of Carbohydrate versus Fat in the Rat", by Trout et. al., published in the Journal of Nutrition; 107: 104-111, 1977, it was determined that "gravity tends to hold back the fat from leaving the stomach, allowing glucose in aqueous solution to be preferentially emptied" and further that "a sizable portion of the starch in starch-containing meals became suspended in water during and shortly after being ingested, and the starch suspension was then emptied from the stomach preferentially to fat-containing particulate matter". It would appear that this functionality of the natural separation of the glucose, or solubilized sugars, as well as the suspended starches and the subsequent acceleration of these components through the pyloric valve into the Duodenum could be eliminated and thereby prevent the blood sugar from elevating while not inhibiting the absorption of the necessary dietary nutrients that are critical to cellular survival.

There remains a need for a less invasive and reversible method of altering patients eating behavior while reducing the dietary impact of foods that are incompatible with diabetic metabolic disorders. There have been attempts in this art to provide medical devices and procedures to address this need.

In U.S. Pat. No. 4,398,910, Blake, et. al. discloses a device for providing drainage from a surgical wound during the post-surgical period of healing.

In U.S. Pat. Nos. 4,501,264; 4,641,653 and 4,763,653; Rockey, discloses medical sleeve devices for placement in a patient's stomach. The medical sleeve described in these patents is intended to reduce the surface area available for absorption in the stomach without affecting the volume of the stomach nor will the described device isolate ingested food from stomach secretions. The medical sleeve is not configured to be deployed in a patient's small intestine and will not have an appreciable impact on the digestion of the ingested food.

In U.S. Pat. No. 4,134,405, Smit, U.S. Pat. No. 4,315,509 Smit, U.S. Pat. No. 5,306,300 Berry, and U.S. Pat. No. 5,820,584 Crabb, sleeve devices are described and are intended to be placed at the lower end of the stomach and therefore do not serve to isolate ingested food from the digestive secretions of the stomach. These sleeve devices are not configured to be deployed in a patient's stomach or to effectively reduce the volume of the patient's stomach or small intestine.

In U.S. Patent Application US 2003/0040804, Stack et al. describe a satiation device to aid in weight loss by controlling feelings of hunger. The patent application describes an antral tube that expands into the Antrum of the stomach to create a feeling of satiation. The devices described are not configured to isolate ingested food and liquids from digestive secretions in the stomach or the intestines.

In U.S. Patent Application US 2003/0040808, Stack et al. describe a satiation device for inducing weight loss in a patient that includes a tubular prosthesis positionable at the gastroesophageal junction region, preferably below the z-line. The prosthesis is placed such that an opening at its proximal end receives masticated food from the esophagus, and such that the masticated food passes through the pouch and into the stomach via an opening in its distal end. The pouch serves to delay the emptying of food into the stomach, thereby providing the patient a sense of fullness prior to filling the stomach.

In U.S. Patent Application US 2003/0093117, Sadaat describes an implantable artificial partition that includes a plurality of anchors adapted for intraluminal penetration into a wall of the gastro-intestinal lumen to prevent migration or dislodgement of the apparatus, and a partition, which may include a drawstring or a toroidal balloon, coupled to the plurality of anchors to provide a local reduction in the cross-sectional area of the gastro-intestinal lumen. The reduction in the cross-sectional area of the lumen delays motility of ingested food, thereby increasing the sense of satiety that the patient experiences.

In U.S. Patent Application US 2003/0120265, Deem et al. describe various obesity treatment tools and methods for reducing the size of the stomach pouch to limit the caloric intake as well as to provide an earlier feeling of satiety. The smaller pouches may be made using individual anchoring devices, rotating probes, or volume reduction devices applied directly from the interior of the stomach. A pyloroplasty procedure to render the pyloric sphincter incompetent and a gastric bypass procedure using atraumatic magnetic anastomosis devices are also described.

In U.S. Patent Application US 2003/0144708, Starkebaum describes methods and systems for treating patients suffering from eating disorders and obesity using electrical stimulation directly or indirectly to the Pylorus of a patient to substantially close the Pylorus lumen to inhibit emptying of the stomach.

In U.S. Patent Number 2014/0275747, Connor discloses a device that is comprised of two passages for food to travel through a patient's digestive tract, referred to as an Adjustable Gastrointestinal Bifurcation. The device has two openings that are regulated by a flow control member that may at least partially direct ingested food into either opening. The bifurcated device is comprised of two openings that are located at the superior end of the device just below the esophageal sphincter. The flow control member is capable of adjustment from a remote location and may direct food into either a passage that enables little absorption of nutrients or a second passage that limits the absorption of nutrients. While the device can divert various food types, it requires a conscious effort on behalf of the user or physician to set the diversion pathway into the correct location for the specific food type that has been ingested. An alternative form of the device requires the implantation or use of a remote sensor within the upper GI tract to sense the type of food being ingested to direct the flow control member. This would require the presence of an invasive foreign object within the upper GI tract, particularly the oral cavity, which would be intolerable to the patient.

In U.S. Pat. No. 7,794,447, Dann, et. al. describe a bypass-type tubular device that may be produced with valves and restrictors to control the exposure of ingested food from digestive secretions. The devices as disclosed form a passage between the upper portion of the stomach, or lower portion of the esophagus, through which ingested food particles will pass. The passage may be produced with valves, or increased porosity, that enables digestive secretions to enter the passage to digest the food contained therein and enables reverse passage of partially digested nutrients to flow back into contact with the absorptive tissues of the GI tract. The restrictive passage may extend as far as the ileum to allow the discharge of partially digested material into portions of the GI tract that may respond and cause the body to eliminate the undigested food from the GI tract. The device, as disclosed, does not differentiate between healthy and unhealthy ingested materials and primarily functions to limit the digestive processes. In the most restrictive form of the device, difficult to digest materials, such as complex proteins, would pass undigested into the ileum and therefore be eliminated from the body without imparting any benefit to the patient.

In U.S. Pat. No. 8,845,674, Brister et. al. describe an inflatable intragastric device that is intended to stimulate a sense of satiety through the introduction of a volume occupying balloon-type device. The device may be orally administered, with an inflation catheter attached in some forms, while self-inflating in other forms, and is preferentially filled with gas to enable the volume occupying device to remain buoyant within the gastric contents. The device is delivered, initially filled, and is subsequently retrieved through an endoscopic procedure once a sufficient weight loss has been demonstrated or period of time has elapsed. Based upon the efficacy of the initial placement, multiple balloons may be installed in an effort to occupy greater space within the stomach. The device provides pressure within the stomach as excess food is ingested, however, the device does not provide differentiation between healthy and unhealthy food selections which enables the subject to defeat the efficacy of the device by preferentially selecting unhealthy calorie dense food options to occupy the remaining space within the stomach.

In U.S. Pat. No. 8,814,898, Gaur, et. al. describe an ingestible, inflatable volume occupying device, a balloon, with a filling catheter attached that is self-deflating. Similar to the balloons disclosed in the Brister patents, the device is delivered in a pill format with the uninflated balloon compacted within the pill capsule. In the compacted form, there is a fine catheter attached that is sized to extend from the patient's mouth upon ingestion. A sterile fluid is delivered through the catheter extending from the oral cavity to inflate the volume occupying device. Unlike the Brister device, the balloon is produced with a feature that provides for self-deflation. The device is produced with an invaginated section that is held secure by a degradable element that is isolated from the abdominal contents, however, it is immersed in the filler fluid. The exposure of the securement element to the filler fluid causes a slow degradation of the element until the strength of the element can no longer maintain the closure of the balloon and releases. The filler fluid is then released from the balloon and the entire structure collapses for passage through the pylorus. While the balloon provides a means to overcome the need to retrieve the balloon after the necessary treatment is complete, as with the Brister device, it only provides the patient with a volume occupying device the provides no selectivity to healthy eating versus high calorie easily absorbed unhealthy options.

Accordingly, there remains an unmet and pressing need to provide a device that is capable of re-directing the most damaging components of food which is ingested, that is reversible, that does not inhibit the digestion of the healthy components of ingested food, that does not rely on patient inputs to function properly, and that provides negative biological feedback to inhibit the ingestion of simple sugars and carbohydrates.

SUMMARY OF THE INVENTION

Therefore, a novel passive caloric bypass device is disclosed. The passive caloric bypass device has an inflatable separative collection element having a structure with a proximal end and a distal end. The structure has at least one longitudinal fluid channel and at least one fluid entry opening in communication with each fluid channel, and the structure has a hollow interior chamber for receiving an inflation fluid to place the structure into an expanded state. The device has a distal transport member having a proximal end and a distal end in fluid communication with the collection element, wherein the proximal end of the transport element is mounted to the distal end of the collection element. A proximal expansion member is mounted to the proximal end of the collection element. And, a distal expansion element mounted to the distal end of the collection element.

Another aspect of the present invention is a novel passive caloric bypass device. The passive caloric bypass device has a separative collection element having a structure with a proximal end and a distal end. The structure has at least one longitudinal fluid channel and at least one fluid entry opening in communication with each fluid channel. The device has a distal transport member having a proximal end and a distal end in fluid communication with the collection element, wherein the proximal end of the transport element is mounted to the distal end of the collection element.

Additional aspects of the present invention include methods of treating obesity using the above-described passive caloric bypass devices.

These and other aspects and advantages of the present invention will become more apparent from the following description and accompanying drawings.

DETAILED DESCRIPTION OF THE INVENTION

Figure 1:
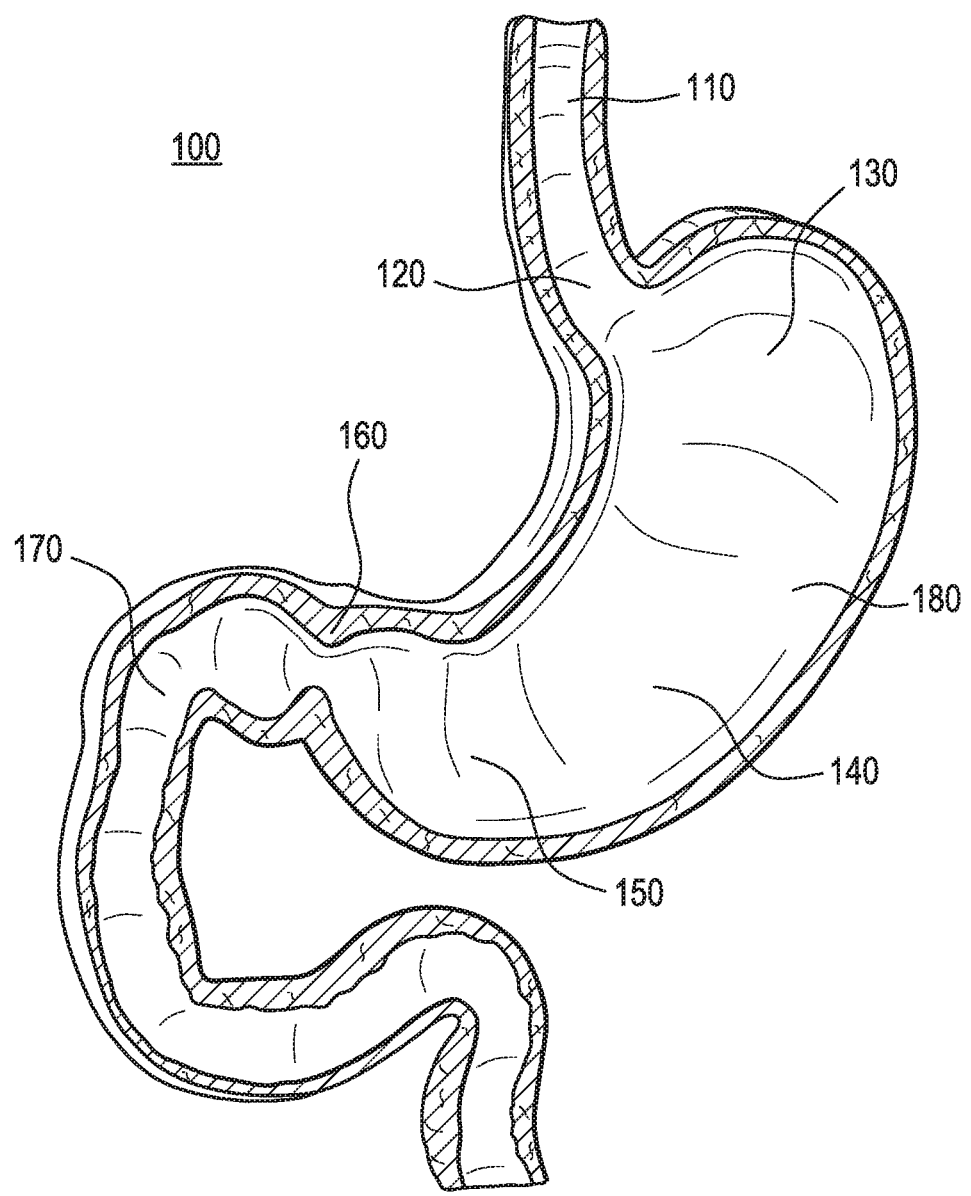
FIG. 1 is a cross-sectional view of a schematic diagram of the upper middle portion of the human gastrointestinal tract.

Referring to FIG. 1, the upper middle portion of the human gastrointestinal tract 100 is illustrated. The esophagus 110 leads to the lower esophageal sphincter 120. The lower esophageal sphincter 120 is located at the entry point into the stomach 180 and serves to admit ingested particles of food (not shown) into the stomach 180 and to subsequently form a seal, when constricted, to prevent the regurgitation of food particles and digestive fluids into the esophagus 110 during the muscular contractions associated with the digestive process. The ingested food enters the stomach 180 near the Fundus 130 and is subjected to the digestive secretions of the stomach lining. As the digestive contractions of the Fundus 130 occur, the food passes towards the Antrum 140 and ultimately passes into the Pylorus 150 of the stomach 180 where it is subjected to strong contractions and the liquefied portion of the semi-digested material, or chyme, is passed into the Duodenum 170 through the dilation of the Pyloric valve 160.

Figure 2:
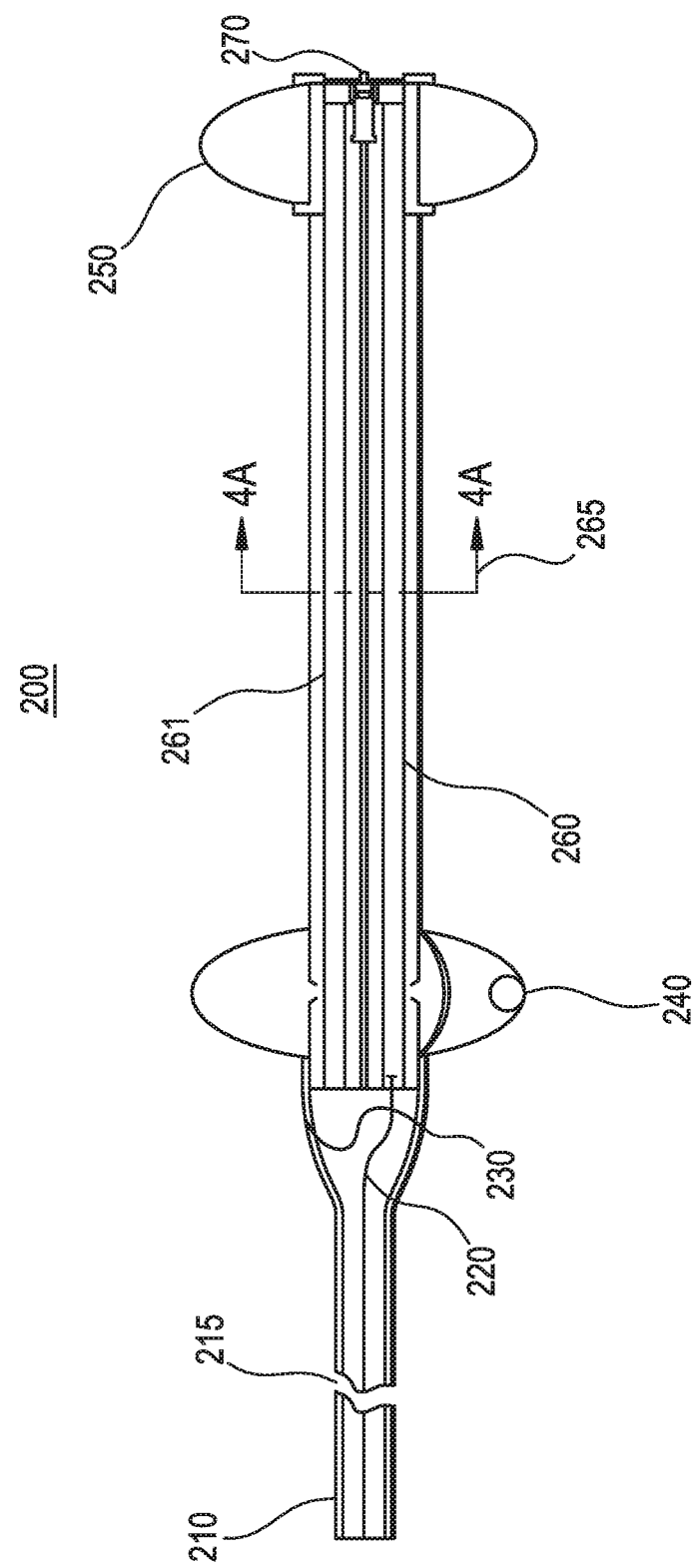
FIG. 2 is a side view of a passive "catheter" style collection device of the present invention; the device has an "inflatable catheter" style.

Referring to FIG. 2, an embodiment of an "inflatable catheter" style passive collection device 200 of the present invention is illustrated. The "inflatable catheter" style passive collection device 200 is comprised of an inflatable central collection element 260, with collection channels 261, which is attached at the proximal end to a proximal expansion element 250, and near the distal end to a distal expansion element 240, with the furthest distal end attached to a transitional collection element 230 which is engaged with a distal transport element 210. Within the proximal expansion element 250 is located an engagement element 280 that, in combination with a fluid transport element 270, enables alteration of the central collection element 260 and the expansion elements 240 and 250 during deployment of the device 200.

The distal transport element 210 is fabricated as an easily collapsible tube having a lumen that is intended to pass through the pyloric valve 160 in the stomach 180 when the device 100 is in the deployed condition. The distal transport element 210 is sized to a length that is determined to be clinically relevant to enable materials contained within the element to bypass at least a portion of the duodenum 170 without contacting other materials or secretions within the duodenum 170. The distal transport element 210 may be produced as an extruded form of thin-walled biocompatible conventional elastomeric or non-elastomeric materials such as silicone, polyurethanes, polyolefins, pvdf, eptfe or other such materials such as natural or latex rubber. The materials must be compatible with the digestive secretions in the gastrointestinal system and resistant to degradation. Alternatively, the materials may be produced as a flat film structure that is folded and welded along a single or along multiple seams to form an enclosed lumen. The use of cast films enables the use of various classes of biocompatible conventional thermoplastic elastomers such as Styrenic block copolymers (TPE-s), Thermoplastic olefins (TPE-o), Elastomeric alloys (TPE-v or TPV), Thermoplastic polyurethanes (TPU), Thermoplastic copolyester, Thermoplastic polyamides. The use of the flat films ensures that the distal transport element 210 will preferentially collapse into a flattened state to minimize the cross sectional area of the deployed element when materials are not passing through it. Alternatively, it may desirable to reduce the size of the "inflatable catheter" style passive collection device 200 prior to elimination of the device from the patient. In such cases, the distal transport element 210 may be produced as a segmented or composite structure. The distal transport element 210 may utilize segments that are produced from absorbable or degradable polymeric materials that are bonded to, or combined with, non-degradable elements to form the complete distal transport element 210. In the segmented structure, the absorbable elements may serve as degradable structural connections of portions of the distal transport element 210. In use, the degradable structural connections will subsequently degrade and enable the non-degradable elements to release from the distal transport element to facilitate passage of the smaller segments from within the gastrointestinal tract. Optionally, a flexible small cross sectional area fiber-like element 220 may be included within the lumen of the distal transport element 210. The inclusion of the fiber-like element 220 ensures that the distal transport element 210 cannot substantially or significantly kink when bent and therefore the lumen of the transport element 210 will remain open for materials contained within the element to pass freely. The distal end of the distal transport element 210 is open and free to the passage of materials from within the element 210 to exit the "inflatable catheter" style passive collection device 200 and re-enter the digestive tract at a location distal to the area to be bypassed, such as the duodenum 170.

The proximal end of the distal transport element 210 may optionally be connected to a transitional collection element 230. The transitional collection element 230 has a distal end and a proximal end. The proximal end may be sized to receive the distal end of the central collection element 260 which may be larger in cross-sectional area than the distal transport element 210. Alternatively, the distal transport element 210 may connect to a collection element that is of similar cross-sectional size as the distal transport tube 210. Alternatively, the transitional collection element 230 may be sized to connect a distal transport element 210 that is larger in cross sectional area than the central collection element 260.

The distal expansion element 240 is attached near the distal end of the of the central collection element 260. The distal expansion element 240 may be produced in a variety of geometric shapes including spherical, toroidal, oval, etc. as may be determined to be suitable to the functional requirements within the typical anatomical geometry surrounding the intended deployment position. The distal expansion element 240, as illustrated, is attached in sealed communication to a portion of the central collection element 260. The distal expansion element 240, as illustrated, in one embodiment is in the form of an inflatable element that may be formed of a thermoplastic elastomeric material, silicones, natural rubbers or other easily expandable conventional materials. Alternatively, the inflatable expansion element 240 may be produced from non-expansible polymeric films that are capable of withstanding the mechanical abrasion and chemical exposure to contents of the digestive tract. The use of non-expansible films to produce a suitable inflation element may require production methods for bonding multiple layers of film together such as energy based or solvent based production methods or through the use of intermediary bonding elements such as glues or stitching.

In the illustrated embodiment of the "inflatable catheter" style passive collection device 200, the central collection element 260 is an inflatable device that has been produced through the use of an extruded profile which will be detailed. The cross-sectional view 265 of the collection element is illustrated as section A-A. The proximal end of the central collection element 260 is bonded to the distal portion of the inner lumen of the proximal expansion element 250. The engagement element is bonded to the proximal portion of the inner lumen of the proximal expansion element 250. The fluid transport element 270 is in selective fluid communication with the proximal end of the central collection element 260 or the proximal expansion element 250 through the inner passages of the engagement element 280.

Figure 3:
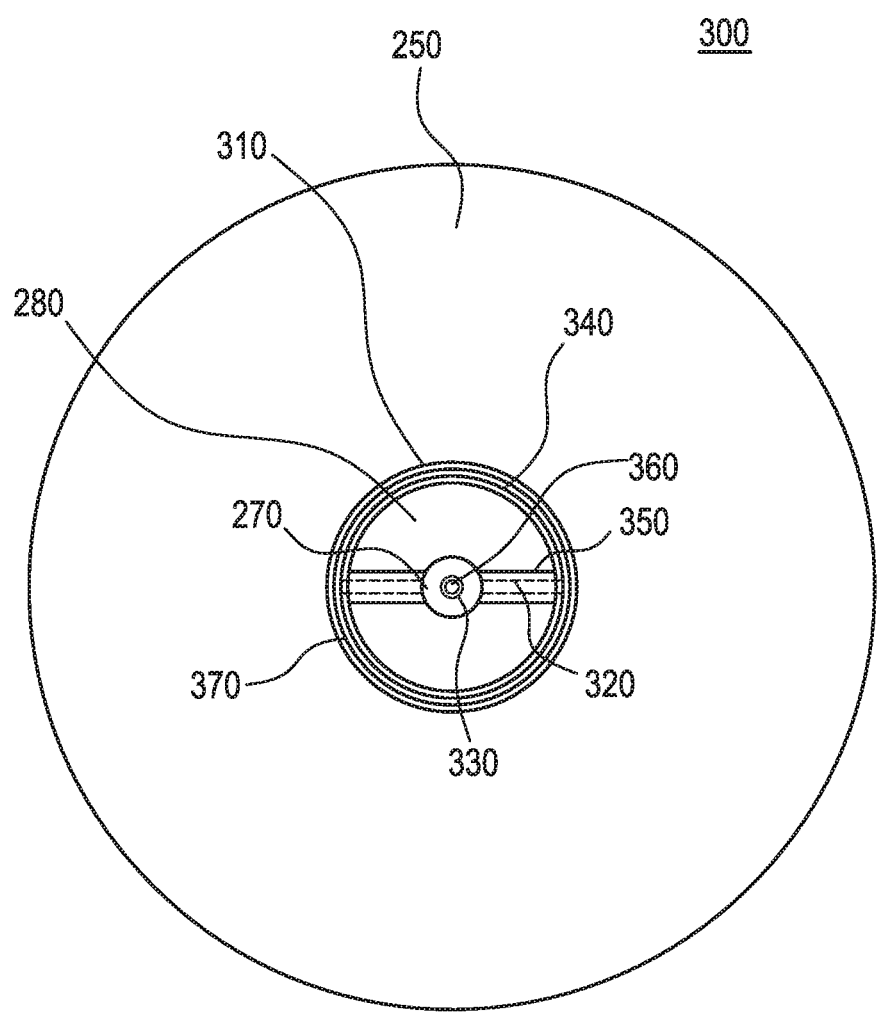
FIG. 3 is an end view of the "inflatable catheter" style passive collection device of FIG. 2.

Referring to FIG. 3, the proximal end of the passive collection device 300 is illustrated. The central portion of the engagement element 280 is covered by the distal end of the fluid transport element 270. The distal end of fluid transport element 270 is bonded to a fluid delivery element 330, which is in the form of a tube that is impermeable to fluids including sterile water and air. At least a portion of the perimeter of the engagement element 340 is in fluid communication with the central lumen 360 of the engagement element as well as the internal volume of the proximal expansion element 250. The proximal expansion element 250 is produced with a flange 310 that is bonded to the inflation element liner 370. A pair of lateral lumens 320 extend laterally from the central lumen 360 through the wall of the inflation element liner 370 and is denoted by the use of the (dashed) hidden lines 320. The internal shape of the lateral lumen extensions 320 may be of any form capable of receiving gas without inhibiting the transport from the central lumen 360 to the inner chamber of the proximal expansion element 250. In order to minimize the volume of material utilized in the engagement element 280, the outer surface 350 of the lateral lumens 320 is shaped to conform to the inner lumen shape with a uniform thin wall structure.

Figure 4A:
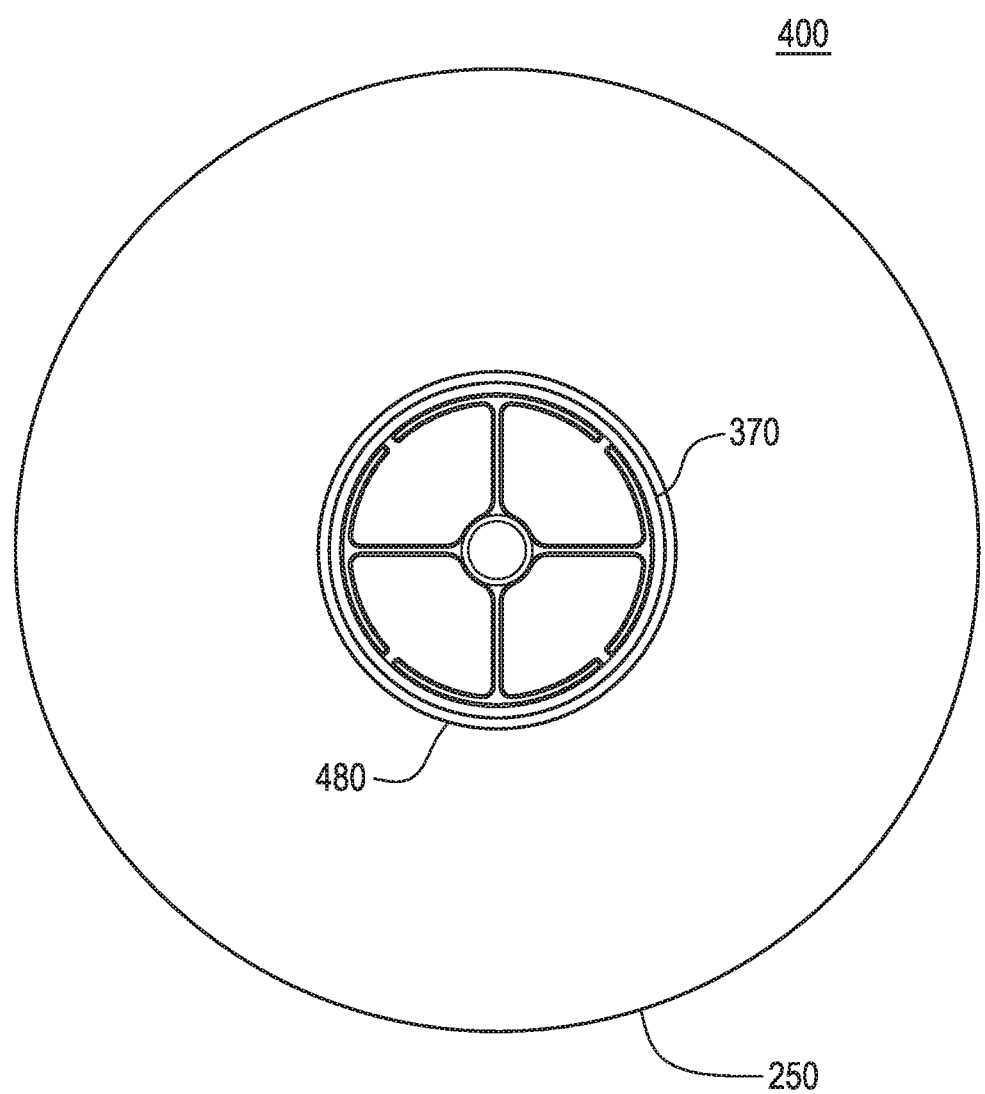
FIGS. 4A and 4B are cross-sectional views of the proximal end of the "inflatable catheter" style passive collection device of FIG. 2.

Referring to FIG. 4A, the cross-sectional view 400 of the proximal end of the central collection element 260 is illustrated. The sectional view shows the cross-section of the collection element 260.

Figure 4B:
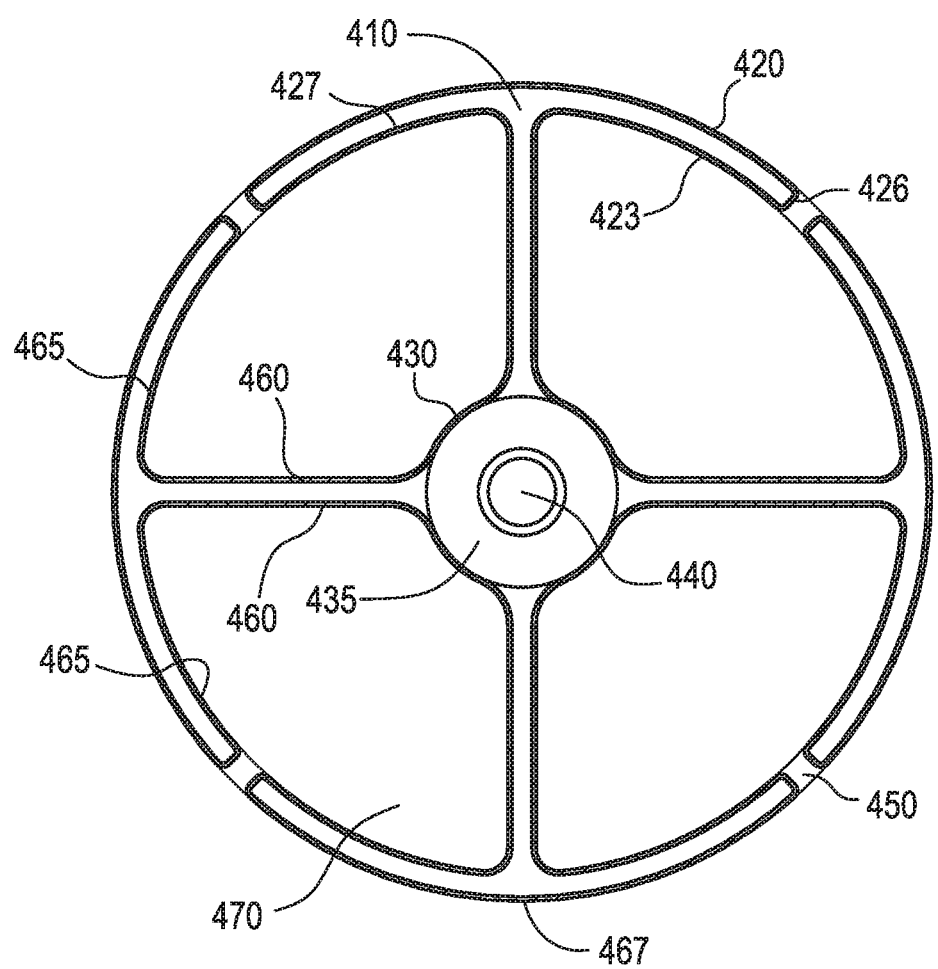

Referring to FIG. 4B, a magnified view of the cross-sectional view 400, Section A-A, is shown for further clarity of the construction of the collection element 260. The central collection element 260 is formed as an extruded thin walled profile with a vacant space 410 within the walls of the formed shape, similar to a balloon. The overall form is illustrated in a generally cruciform shape with an external surface 420 and 423 that is exposed to the external environment and an inner surface 427 that is enclosed within the form. The general form is produced with pairs of extension elements 460 that extend outwardly from a central lumen 440. There are four pairs of extension elements 460 that abut with, and are connected to four pairs of inner perimeter segments 465. Additionally, there are four outer perimeter wall segments 467 that are matched in form with the inner perimeter segments. The inner perimeter segments 465 and the outer perimeter segments are contiguous to each other through the use of radius end elements 423. In an aggregate view of the cross-section of the collection element, it can be seen that the perimeter segments 465 and 467 and the radius end elements 423 form a generally broken circular form with gaps 450 located between each set of perimeter elements and further that each perimeter element is approximately bisected by the paired extension elements 460. The intersection of the inner perimeter elements 465 with the abutting extension elements 460 define a geometrical boundary that is somewhat triangular in form with one side of the triangular form interrupted by the gap 450. Thus, the semi-triangular cross-sectional area forms a contained space in the extruded device that serves as an inner lumen 470. Further, if a line were drawn from any one the vertices of the triangle to intersect perpendicularly with the opposing side, forming an altitude line, it would be noted that the minimum length of any one of the three altitude line segments would be longer then the length of the gap between any two of the proximate radius end elements 423. It can be seen that the presence of the gaps 450 along the length of the previously described thin walled cruciform extruded shape forms the collection channels 261 in the side of the central collection element 260. The four lumens 470 are in fluid communication with the environment that is external to the collection element 260 through the collection channels 261 previously described. It is preferable that the collection channels 261 be sized to permit the ingress of fluids and very fine particulate to the inner lumen 470 portion in fluid communication with the collection channel 261.

The connection of the proximal end of the central collection element 260 with the proximal expansion element 250 is achieved through the contact and bonding of the external wall segments in abutment with the inner surface of the expansion element liner 370. The distal surface of the proximal expansion element 250 is produced with a distal flange element 480 that is in abutment and bonded with at least a portion of the outer surface of the expansion element liner 370.

Figure 5A:
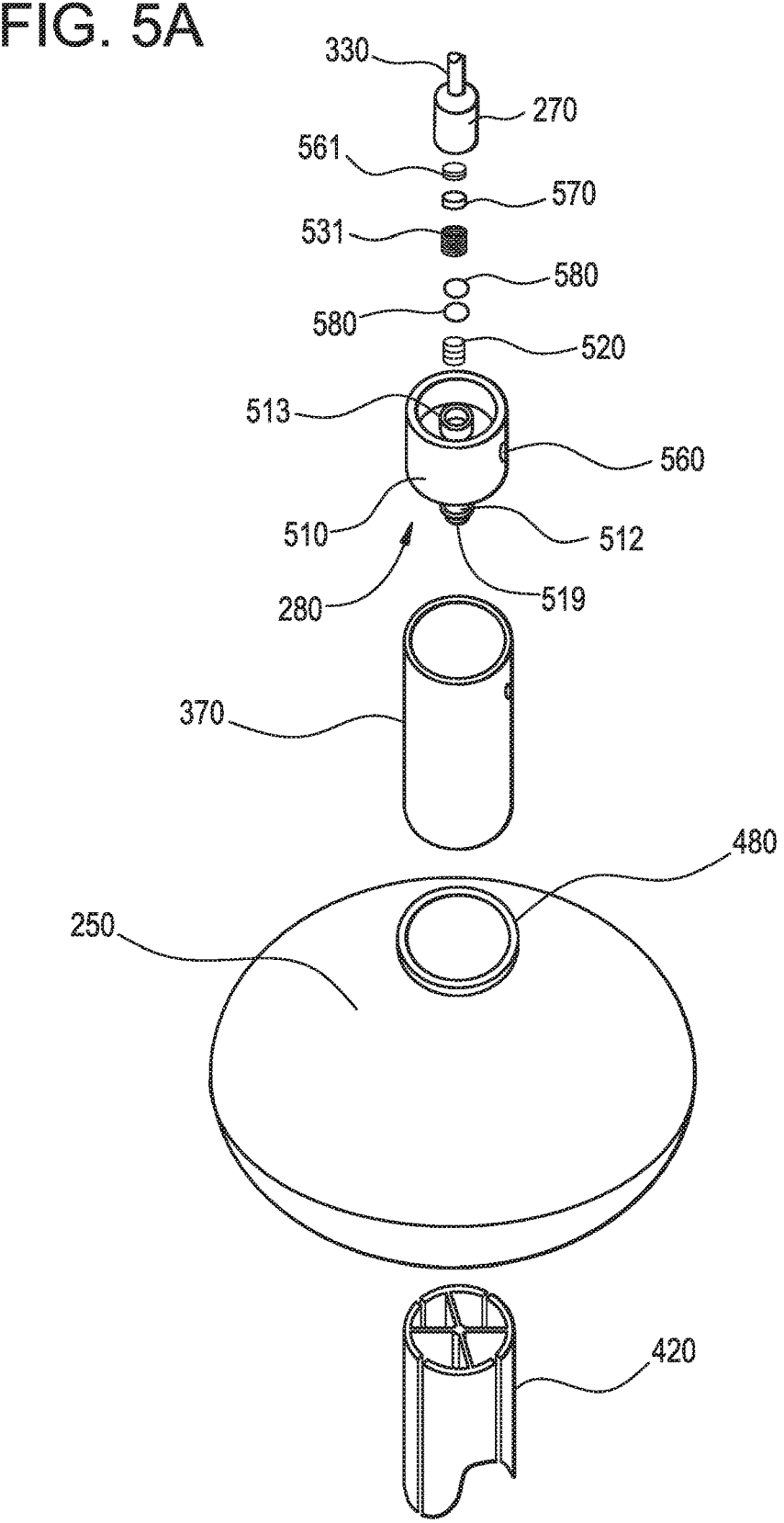
FIGS. 5A through 5C are cross-sectional views of the proximal end and the proximal engagement member and associated assembled components of the device of FIG. 2.

As seen in FIG. 4B and FIG. 5A, the distal face 435 of the barbed type tip 519 is bonded to the inner wall of the collection element central lumen 430 and provides direct fluid communication with the enclosed vacant space 410. The bond may be achieved through the use of energy bonding methods, adhesives, or mechanical compression such as that provided through the use of a suture material wrapped about the inner portion of the collection element. Additionally, while a cruciform structure has been disclosed other forms that provide similar inner channels as well as collection channels along the length of the collection element are feasible. Forms such as bisected oval cylindrical forms, rectangular, square, or other polygonal shapes are feasible and can serve the similar functionality. The use of internal forms such as the cruciform shape may be replaced through the use of interrupted externally self-supported wall forms such as a triangular form with one apex disconnected to form a single collection channel 261 along the length of the collection element 260.

Figure 5B:
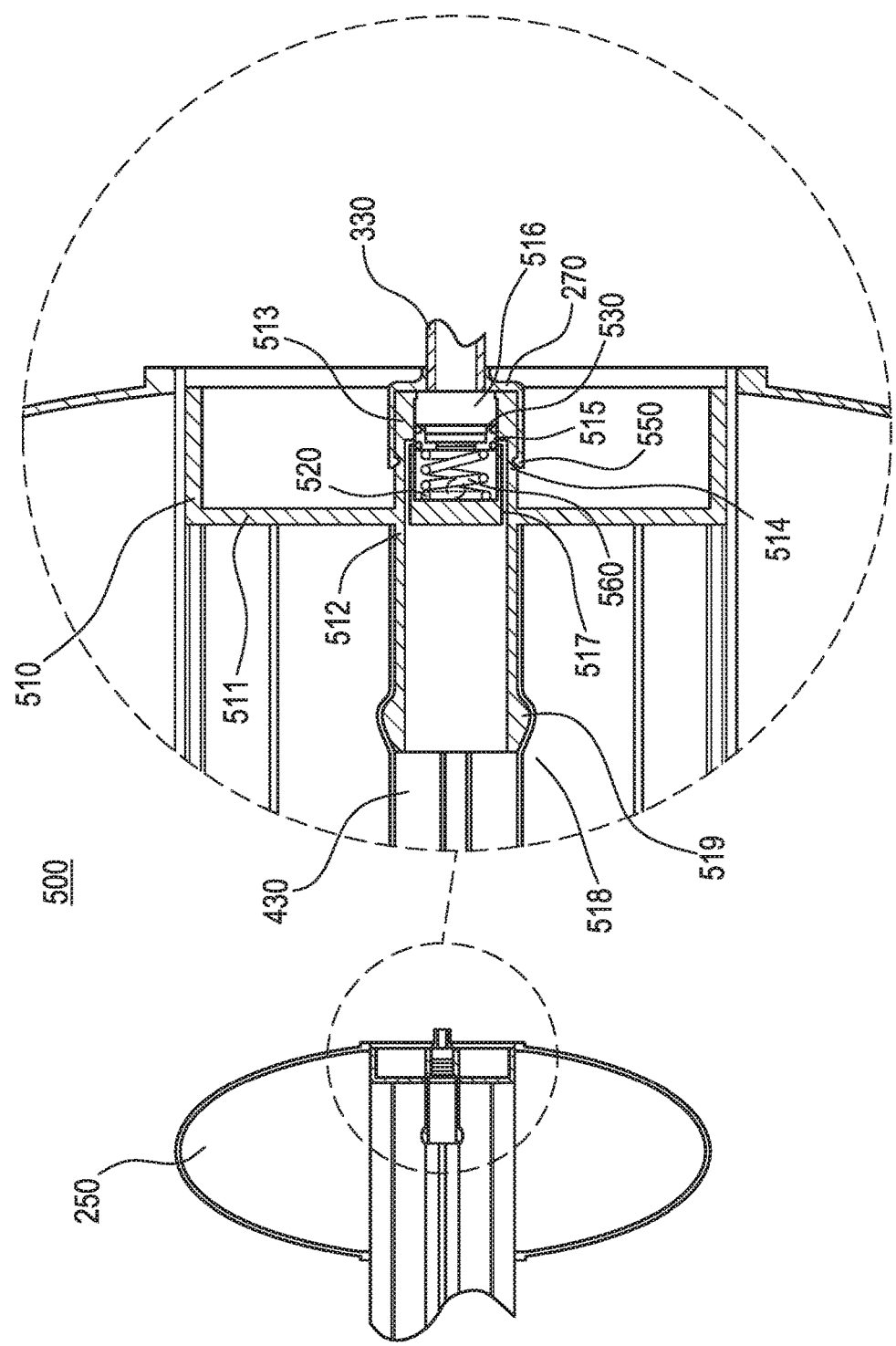
Figure 5C:
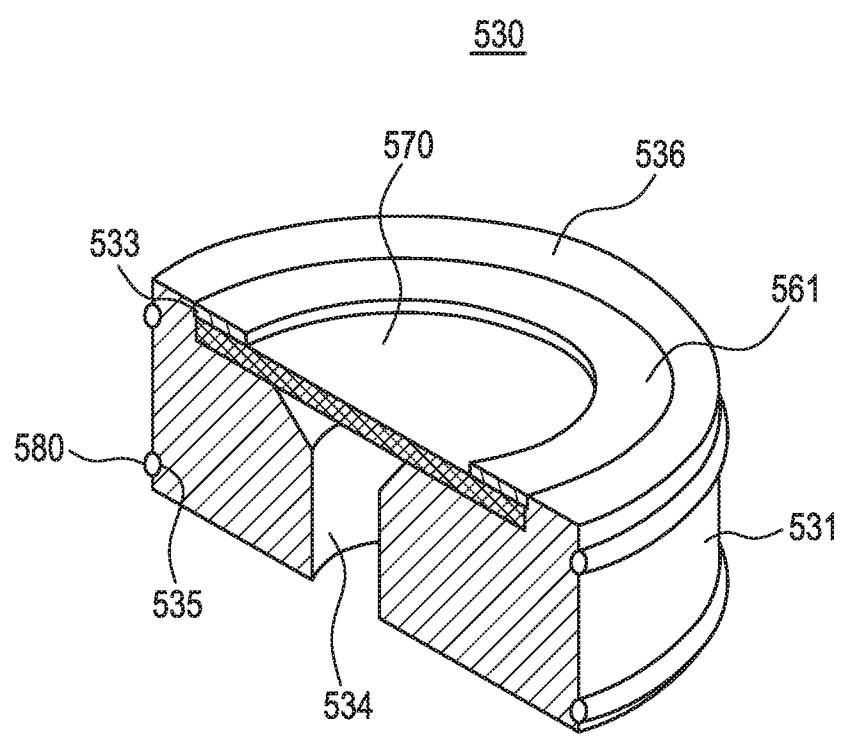

Referring to FIGS. 5A through 5C, a series of views including a cross-sectional view of the proximal end of collection device 200 showing the proximal engagement member 280 and associated assembled components 500 is illustrated. The proximal engagement element 280 (FIG. 2) has a cylindrical side wall element 510 that abuts and connects to a flat disc like element 511 that extends from a central cylindrical engagement element 512. The distal end 518 of the central cylindrical engagement element 512 may include a "barbed" type tip 519 for interfacing with the central lumen of the collection element 430. The proximal end 513 of the central cylindrical engagement element 512 is formed with an external cylindrical shape with a concave ring 514 that extends at least partially about the perimeter of the central cylindrical engagement element 512. While the proximal end 513 of the central cylindrical engagement element 512 is illustrated as a typical smooth surfaced cylinder with the one convex ring structure, other geometries such as convex elevated rib-like ring structure or discrete lug-type engagement elements may be preferred.

The central cylindrical engagement element 512 is produced with a smooth inner bore 516 on the proximal end. At least one axial passage 517 is formed within and parallel to the central axis of the side wall of the central cylindrical engagement element 512. The passage 517 extends from the distal bore of the central cylindrical engagement element 512 up to a lateral passage 515 to provide fluid communication between the distal and proximal bores of the central cylindrical engagement element. In addition to the passages formed within the sidewall and parallel to the axis of the cylindrical engagement element 512, at least one lateral lumen 320 extends radially from the center of the cylindrical engagement element, and is discrete from the axial passages 517. The lateral lumen includes a directional flow element 560 that enables fluid communication from within the proximal bore of the central cylindrical engagement element 512 to a position external to the cylindrical side wall element 510. The lateral lumen exit in the side wall element 510 is aligned with a passage through the inflation element liner 370 which permits fluid communication between the inner contained volume of the expansion member 250 and the smooth inner bore 516 of the central cylindrical engagement element 512 when the components are bonded into position.

Contained within the smooth inner bore 516 of the central cylindrical engagement element 512 is a piston assembly 530 as well as a return spring 520. A partial sectional view of the piston assembly 530 is illustrated as FIG. 5C. The piston assembly is comprised of a carrier barrel 531, two seal elements 580, a filtration membrane 570 and a retainer 561. The carrier barrel is formed from a biocompatible material that may be polymeric or metallic. The carrier barrel is produced with a stepped through bore 534 with an internal geometry for receipt of the filtration membrane 570 as well as the retainer 561. The first step of the inner diameter, near the proximal side of the carrier barrel 531, is produced with a slight undercut feature 533 that serves to lock the retainer into the carrier barrel 531. The retainer element 561 provides a compression of the filtration membrane 570 within the carrier barrel 531 to lock it into position. The filtration membrane 570 is selected with a porosity that is resistant to the passage of fluids, such as sterile water, however allows the passage of air or other gases such as nitrogen or carbon dioxide. Conventional membranes utilized as sterile filters including those produced of ePtfe, etc., are suitable. Two concave channels 535 are located about the perimeter of the carrier barrel and are intended to receive the two seal elements 580. In this embodiment, the seal elements 580 are simple silicone rubber O-rings. Alternative seal members such as bellows or wiper style seals and the like may be utilized as well.

Figure 6:
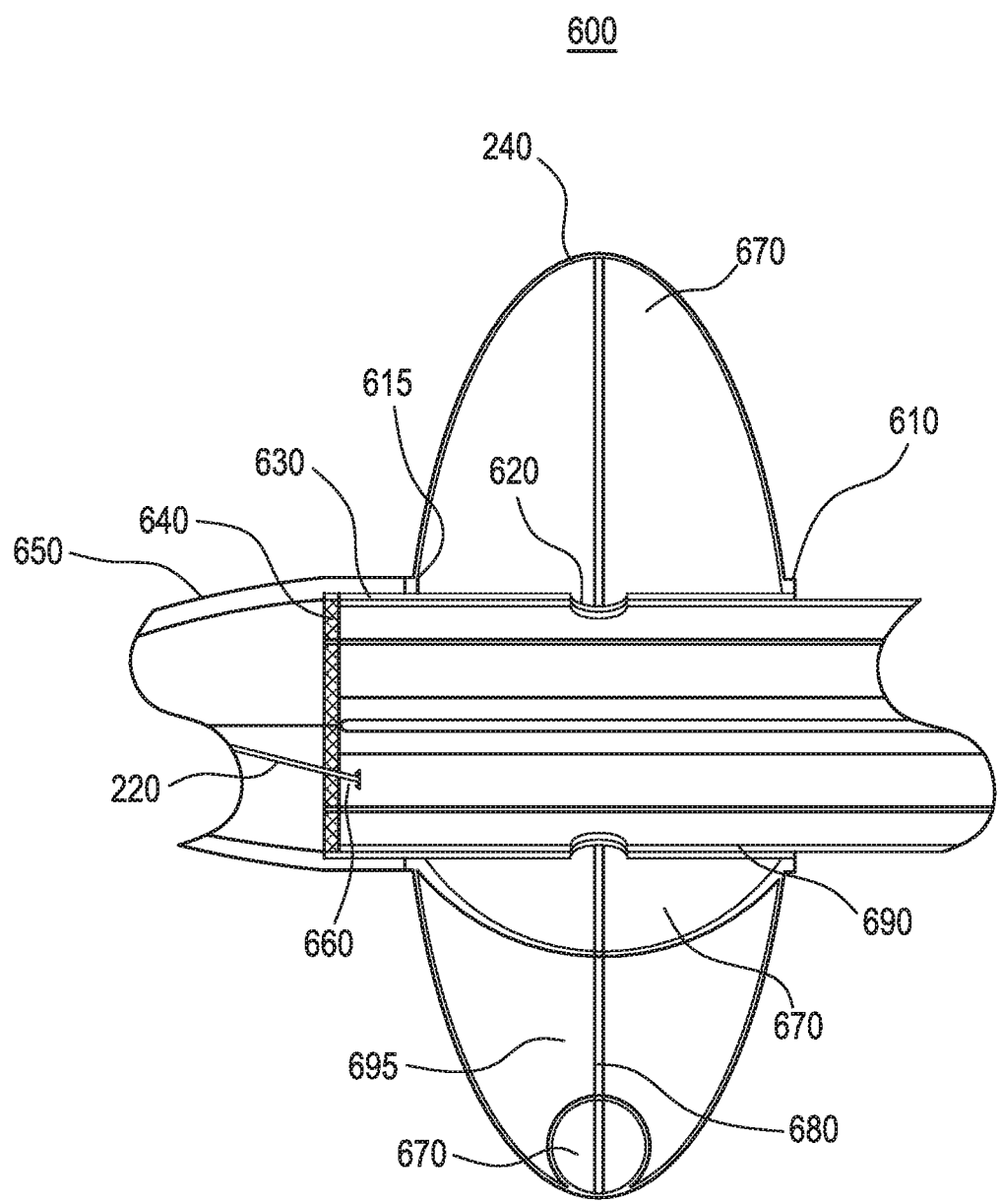
FIG. 6 is a partial cross-sectional view of the distal expansion element of the device of FIG. 2.

Referring to FIG. 6, the distal expansion element 240 is illustrated in a partial cross-sectional view 600. The distal expansion element 240 in this embodiment is an inflatable component and has an enclosed volume 670 and is produced with proximal flange 610 and distal flange 615 and an internal seam 680, since the distal expansion element 240 is formed in two halves that are subsequently bonded together. The distal expansion element 240 is formed with two through passages, 690 and 695. The first through passage 690, located on the proximal half of the distal expansion element 240, receives the distal end of the central collection element 260 and distal expansion element liner 630 that have been inserted and bonded to the distal expansion element 240, and a second through passage 695 in the form of a semi-toroidal shape for the passage of chyme when the element is deployed. The distal end of the enclosed vacant space 410 of the extruded form of the central collection element 260 is sealed and is illustrated as 640. The seal may be created in a conventional manner, for example through the use of energy-based methods such as thermal welding, or alternatively through the use of adhesives or through the application of mechanical means such as compression elements or plug like elements. At least one port 620 is formed through the external wall of the distal end of the central collection element 260 and through the mating portion of the distal expansion element liner 630 to enable fluid communication between the enclosed volume 670 and the enclosed vacant space 410 of the central collection element 260. The distal portion of the distal expansion element liner 630 extends beyond the distal flange 615 of the distal expansion element 240 and extends into, and is bonded to, the proximal portion 650 of the transitional collection element 230. Additionally, the proximal end of the fiber-like element 220 is fastened to the distal end of the central collection element 260 within the distal expansion element 240 through the use of a knot 660. Alternatively, the fiber-like element may be bonded to other features such as the distal end of the distal expansion element liner 630 or to the proximal end of the transitional collection element 230.

Figure 7:
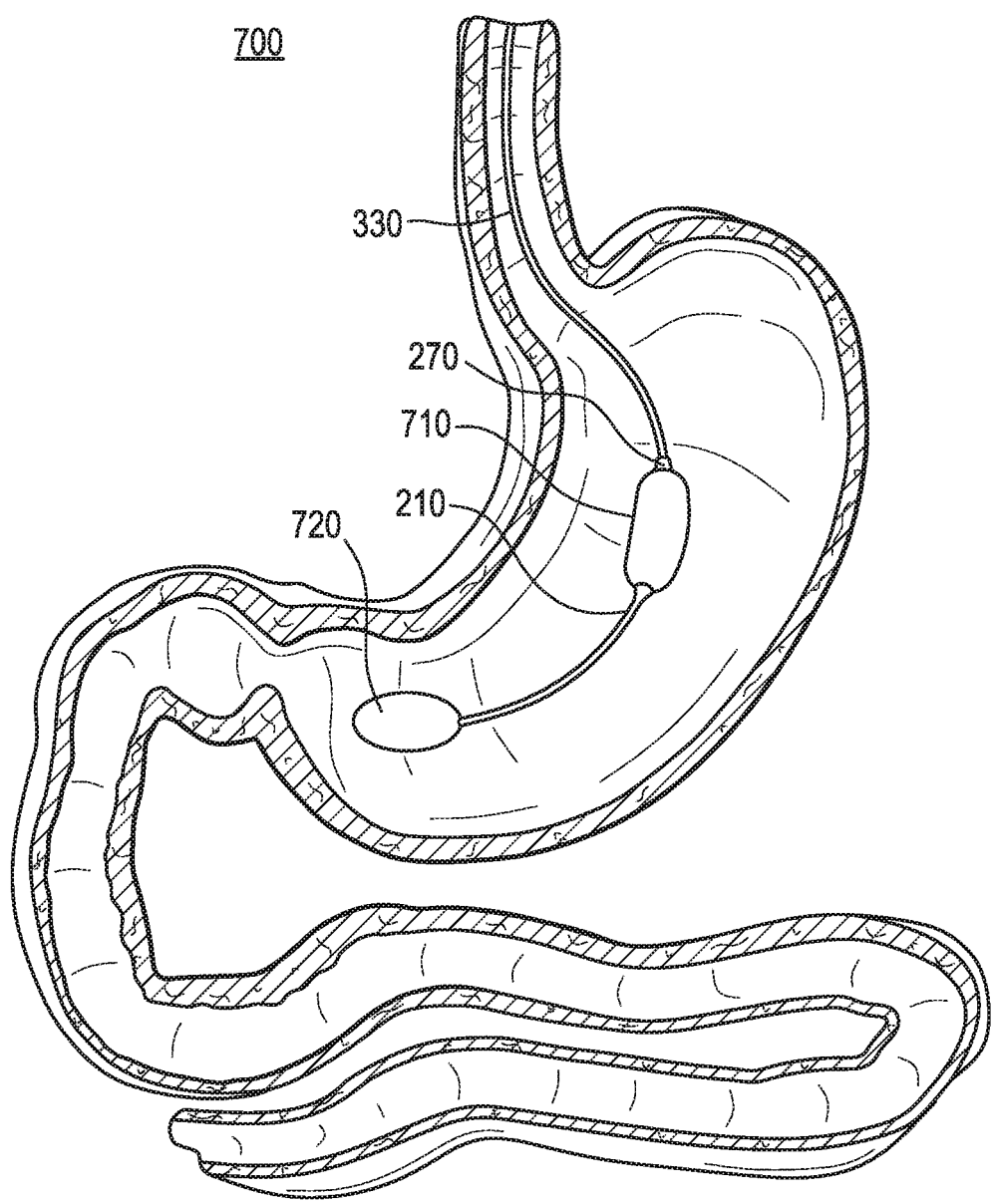
FIG. 7 is an illustration of the device of the present invention in a compacted form and as initially deployed within the gastrointestinal tract.

Referring to FIG. 7, the "inflatable catheter" style passive collection device 200 previously described has been packaged into a compacted form and has been ingested to initiate deployment of the "inflatable catheter" style passive collection device 200 within the gastrointestinal tract. In order to enable easy ingestion of the "inflatable catheter" style passive collection device 200, a portion of the distal transport element 210 has been compacted into a pill form and is contained within the soluble degradable distal capsule 720. In the illustrated embodiment, the central collection element 260 as well as the distal and proximal expansion elements 240 and 250 have been compacted into a soluble degradable proximal capsule 710. The gelatin or capsule material may be produced from materials that are not soluble in water but are readily soluble in the presence of the secretions of the stomach. Alternatively, capsules that are not soluble but structurally are degradable through rupturing or fracturing into fragments when expansion forces are utilized are also feasible. At least a portion of the distal transport element 210 extends between the distal gelatin capsule 720 and the proximal gelatin capsule 710. It may be preferred to produce the compacted "inflatable catheter" style passive collection device 200 with a distance of eight to ten inches between the two capsules to enable easy swallowing without obstructing the epiglottic vallecula prior to the swallowing of the proximal capsule. The fluid delivery element 330 extends from the proximal end of the proximal gelatin capsule 710 and through the lower esophageal sphincter and out of the oral cavity. The fluid delivery element 330 is sized to any desirable length that enables a comfortable delivery of the inflation fluids to the expansion and collection elements. A length of eighteen to thirty six inches may desirable between the proximal opening and the distal end of the fluid delivery element.

Figure 8:
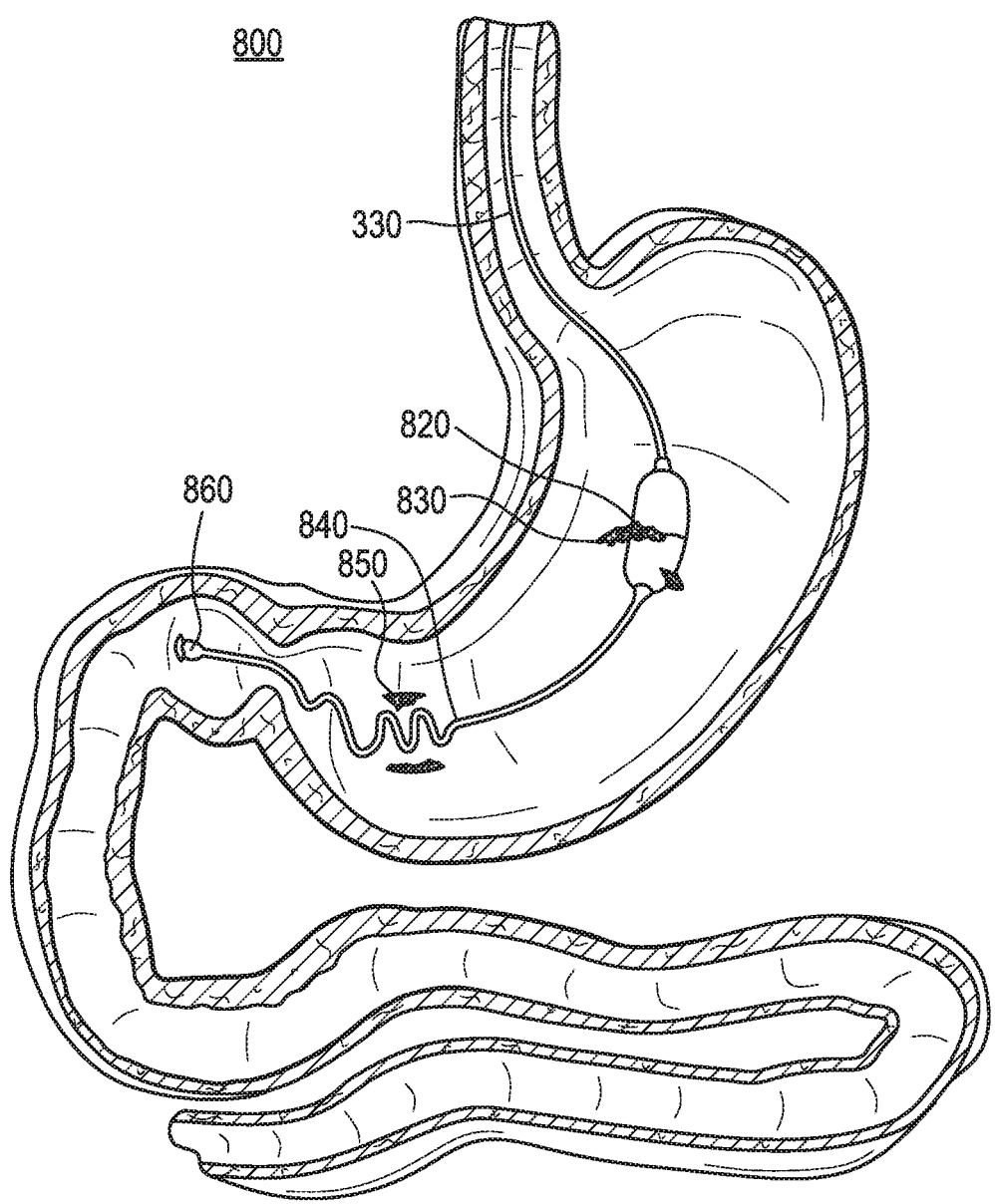
FIG. 8 is an illustration of the device of FIG. 7 in a partially opened state.

Referring to FIG. 8, the initial stages of the "inflatable catheter" style passive collection device 200 progression to final form is illustrated in the partially opened state 800. The distal gelatin capsule is produced with a slightly thinner wall thickness to enable quicker rupture than the proximal capsule. Portions of the solubilized capsule 850 have released from the compacted distal capsule. This difference in dissolution rate of the distal capsule enables the compacted portion 840 of the fluid transport element to expand from the folded or compacted condition. The distal end of the fluid transport element may be produced with a slow dissolving component 860 attached. This slow dissolving element 860 serves as a propagation aid to help the distal end of the fluid transport element to pass through the pyloric valve and to be carried distally towards the ileum through the propagation of the peristaltic contractile waves. It can also be seen that the proximal capsule rupture 820 has initiated and a portion of the compacted "inflatable catheter" style passive collection device 200 has started to emerge from the ruptured capsule.

Figure 9:
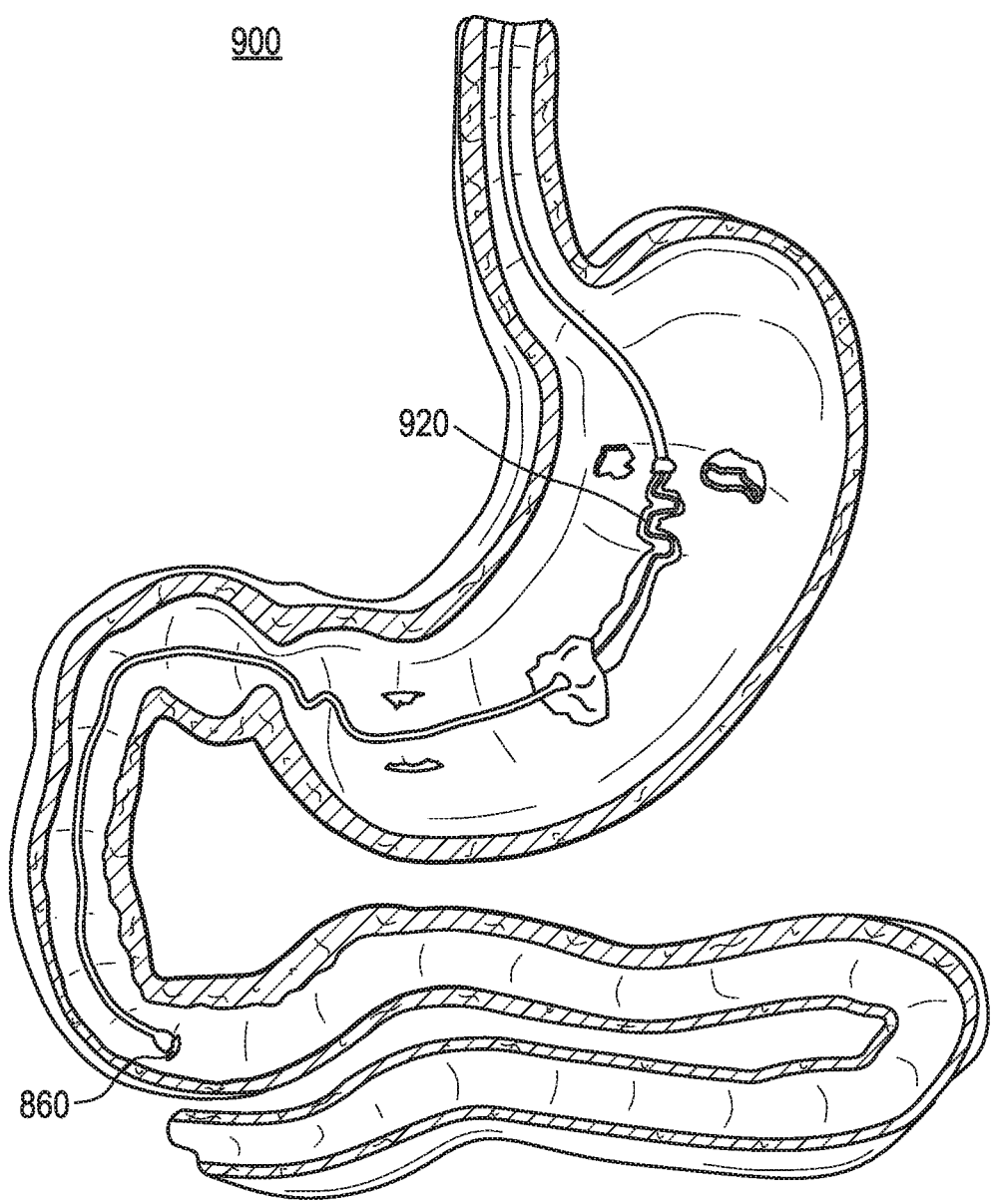
FIG. 9 illustrates the device of FIG. 8 after the continued dissolution or degradation of the capsules has resulted in a full release of the compacted and uninflated proximal portion of the "inflatable catheter" style passive collection device

Referring to FIG. 9, the continued dissolution of the capsules has resulted in the full release of the compacted and uninflated proximal portion of the central collection element 920. As the slow dissolving component attached to the distal end of the fluid transport element has progressed distally towards the ileum, the proximal portion of the central collection element 920 initially unfolds.

Figure 10:
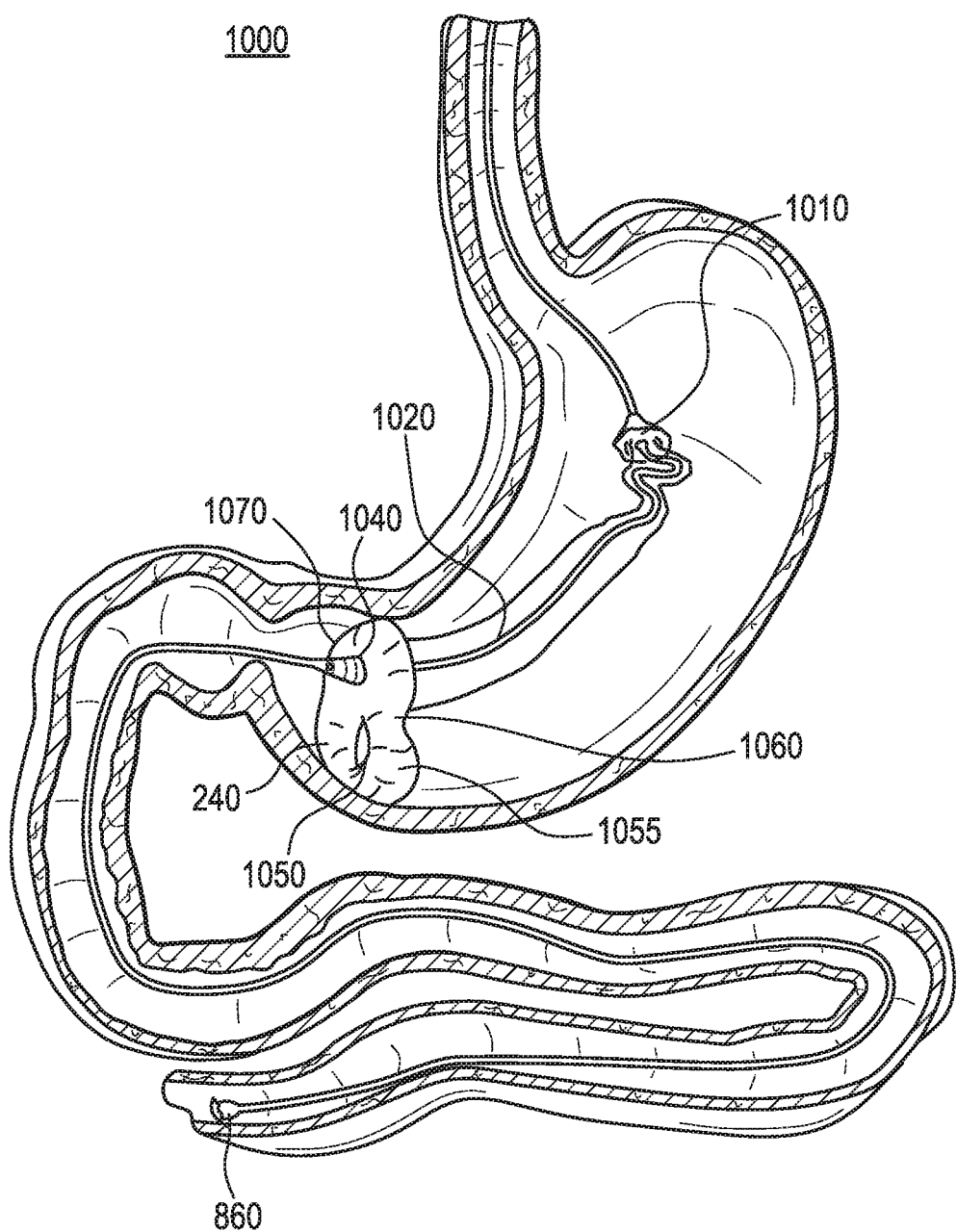
FIG. 10 illustrates the device of FIG. 9 connected to a source of pressurized fluid such that the distal expansion element is in an expanded state.

Referring to FIG. 10, the proximal end of the fluid transport element has been connected to a source of pressurized fluid, such as a syringe, and sterile water has begun to be injected into the proximal end of the collection device. The injection of liquid into the proximal end of the device results in the fluid contacting the piston assembly 530. The piston assembly is resistant to fluid passage through the stepped bore 534 due to the presence of the filtration membrane 570. As the fluid flow from the syringe continues, the pressure builds causing the piston assembly to compress the return spring 520. As the piston assembly is moved distally, the fluid ports of the lateral passages 515 are exposed and results in the fluid passing through the lateral passages and into the inner vacant space within the central collection element 260. As this space is in communication with the inner volume of the distal expansion element 240, the fluid fills the distal expansion element 240 resulting in an expanded form 1070, i.e., the element 240 is in an expanded state ready to perform its function. The outer profile 1060 of the distal expansion element 240 may be preferentially produced in a lobular form 1055 as illustrated, although other forms such as oblong, spherical, etc. may be preferred. The embodiment as illustrated is produced with a passage 1050 for the chyme to pass through, somewhat unobstructed. Once the distal expansion element 240 has filled, the distal portion of the central collection element 1020 begins to inflate. Since fluid is utilized, the tendency of the device to fill from the distal end to the proximal end is likely to occur due to the effects of gravity during filling and the loss of buoyancy. It should be noted that the uninflated proximal expansion element 1010 remains uninflated due to the presence of the filtration membrane preventing fluid passage through the piston assembly.

Figure 11:
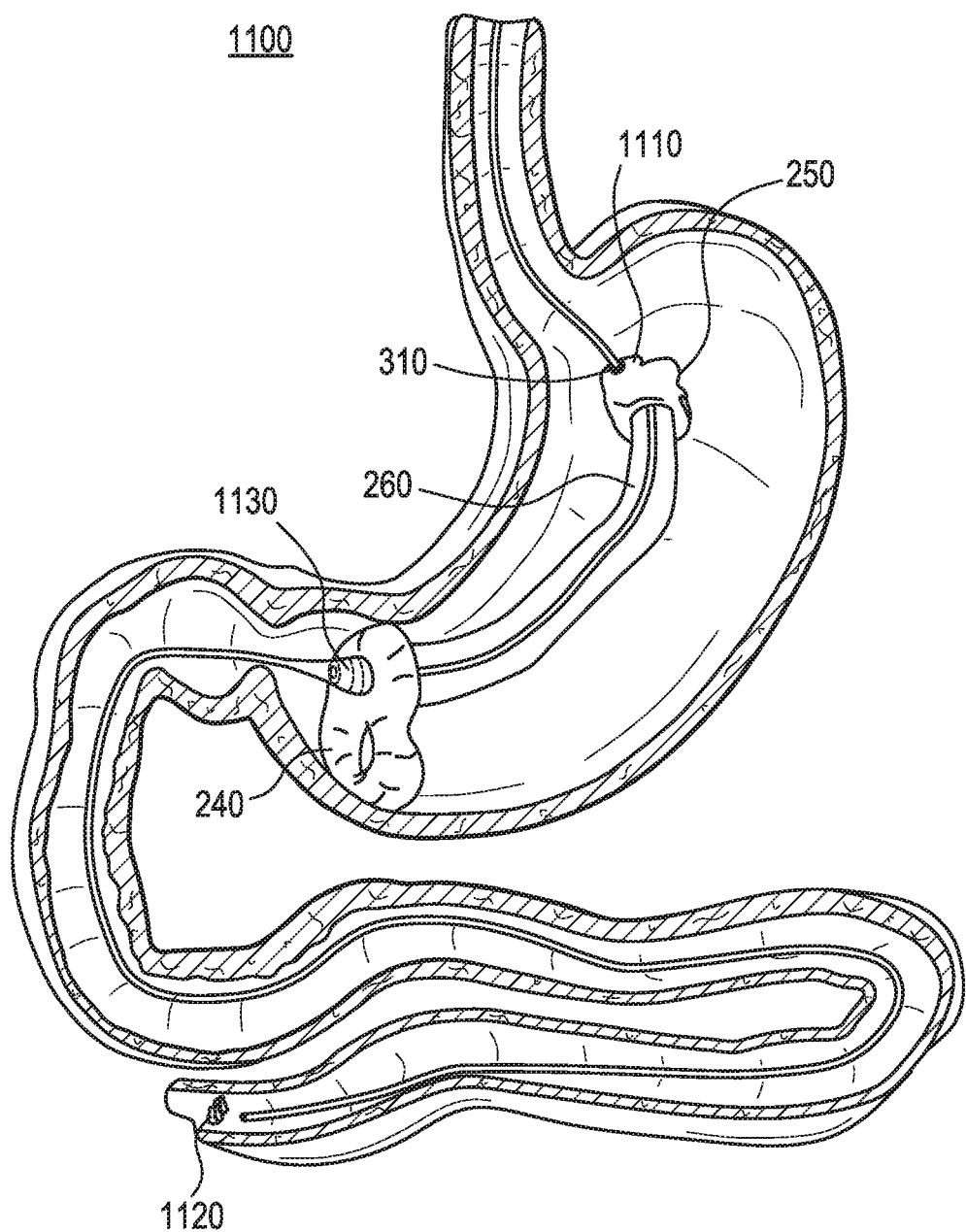
FIG. 11 shows both the central collection element and the distal expansion element in expanded states.

Referring to FIG. 11, the inflation of the central collection element 260 and the distal expansion element 240 has been completed. The completion of the filling operation is detectable as the pressure increases in the fluid during the filling operation as well as the fluid flow rate declines. During this stage of filling, the pressures, both proximal to the piston assembly 530 as well as distal to the piston assembly 530, begin to equilibrate. The fluid application is discontinued and the piston assembly 530 is capable of moving proximally to seal off the lateral passages 515. At this point, the syringe is reversed to withdraw any excess fluid form the delivery element. Alternatively, the distal end of the fluid transport element 270 may utilize a two position sliding motion that enables the fluid to pass out of the distal end of the fluid transport element 270 with air pressure assist. Upon evacuation of the fluid, the proximal end of the fluid transport element 270 is attached to a source of pressurized gas, such as air for example, Nitrogen, $CO_2$ or mixtures thereof. The pressurized gas passes through the filtration membrane and therefore does not cause any motion of the piston assembly. The gas then passes through the directional flow element 560 and causes the inflation of the proximal expansion element 250 to be initiated. The device may optionally include an anti-reflux element 1130 which allows fluid to pass distally, however, it closes when the peristaltic wave is at the same position as the anti-reflux element or is passing distally to prevent regurgitation of fluid into the stomach.

Figure 12:
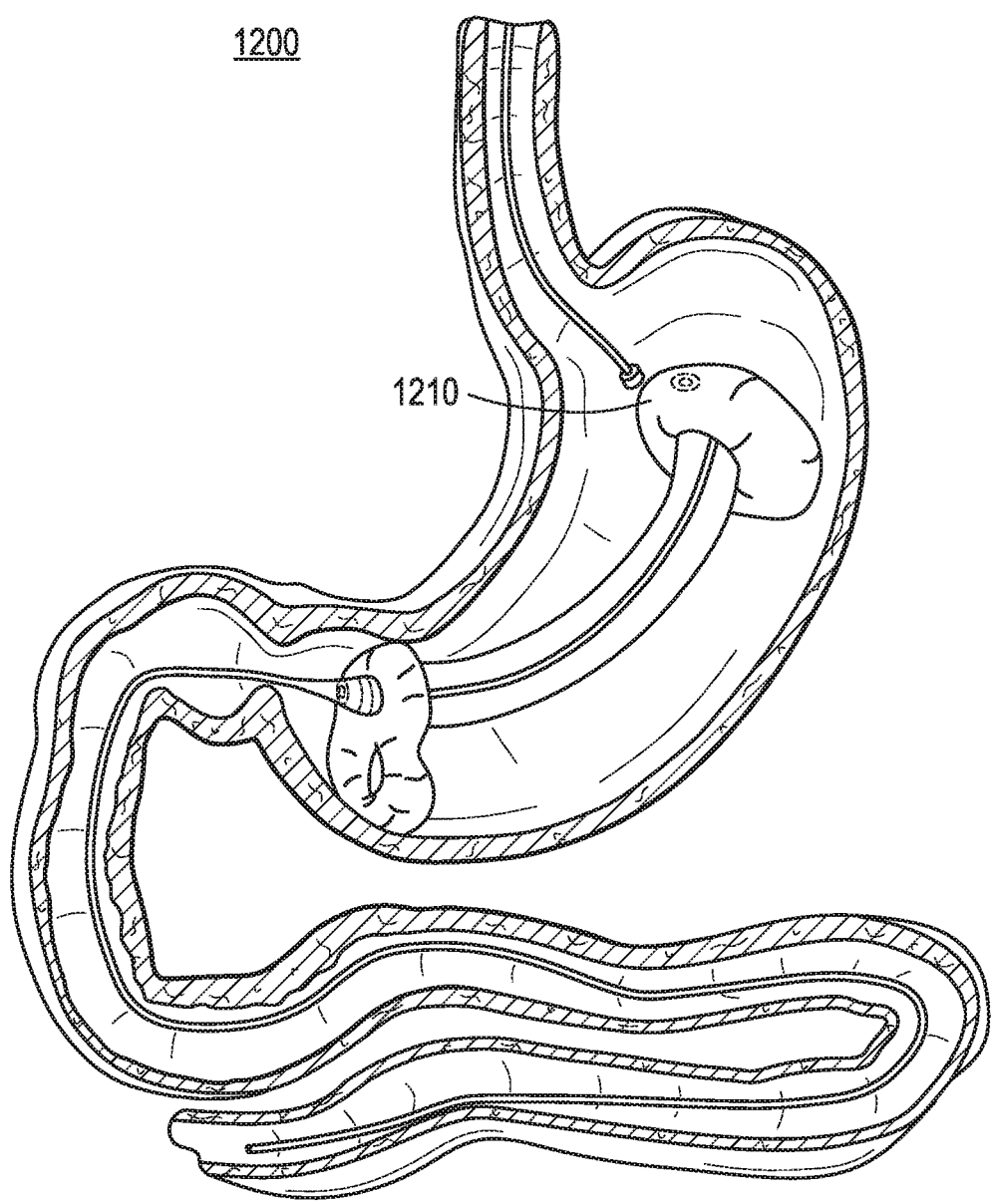
FIG. 12 shows the proximal expansion element fully expanded.

Referring to FIG. 12, the proximal expansion element 250 has been fully expanded though the use of a compressible gas. The pressure in the fluid transport element 270 is increased until the distal end of the fluid transport element 330 expands and disengages from the central cylindrical engagement element 512. Upon this release, the fluid transport element 270 is released from the fully inflated proximal expansion element 1210. Thus the two expansion elements are filled with differing fluids, liquid and gas, to ensure that the "inflatable catheter" style passive collection device 200 is oriented somewhat vertically within the stomach of the patient. Additionally, the proximal expansion element 250 located on the end of the "inflatable catheter" style passive collection device 200 is filled with a compressible gas which helps in compliance with the free end of the collection element to prevent possible abrasion of the stomach wall.

Figure 13:
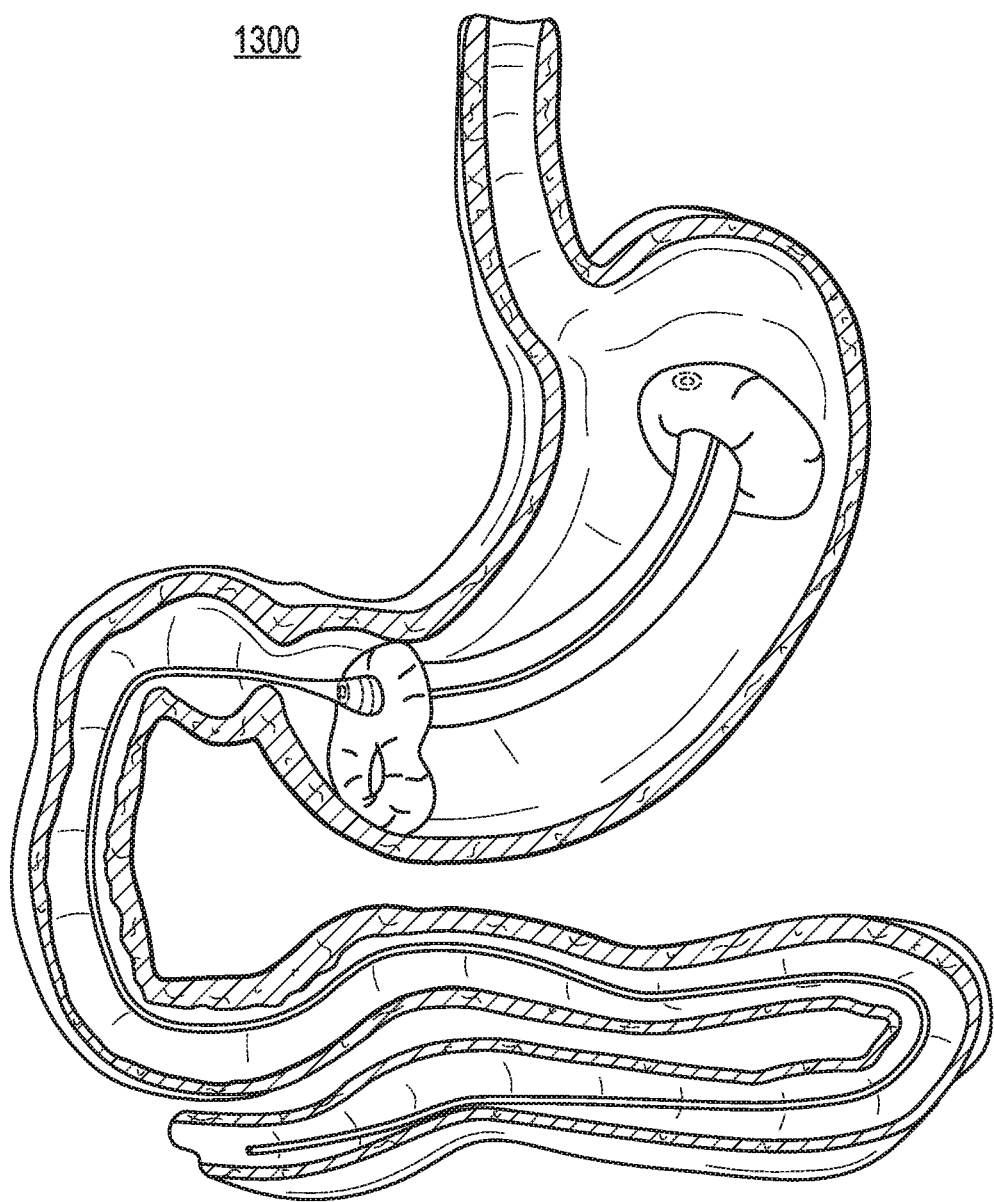
FIG. 13 illustrates the inflated "inflatable catheter" style passive collection device within the stomach compartment and the fluid transport element removed.

FIG. 13 is an illustration of the inflated "inflatable catheter" style passive collection device 200 within the stomach compartment and the fluid transport element 270 removed. While the order of operation previously presented utilized the liquid component first, it may be advantageous to utilize the gas first to float the free end of "inflatable catheter" style passive collection device 200 and then subsequently fill the liquid portion of the "inflatable catheter" style passive collection device 200. In this order of operation, there are additional benefits in that the filtration membrane 570 does not get wet prior to the function of passing the gas through to the proximal expansion element 240, as well as the possibility to utilize high pressure fluid to eject the fluid transport element 270 from the proximal end 513 of the central cylindrical engagement element 512. Thus the inclusion of the piston assembly 530 and mating components, combined with the locations of the lateral passages 515 and the directional flow element 560 enables the pressurization of the various components of the "inflatable catheter" style passive collection device 200 with disparate viscosity fluid mediums, liquid and gas, without co-mingling of the disparate viscosity fluids, within the device, through the creation of distinct fluid communication channels from one common access port and functions as a directional valve assembly.

Figure 14:
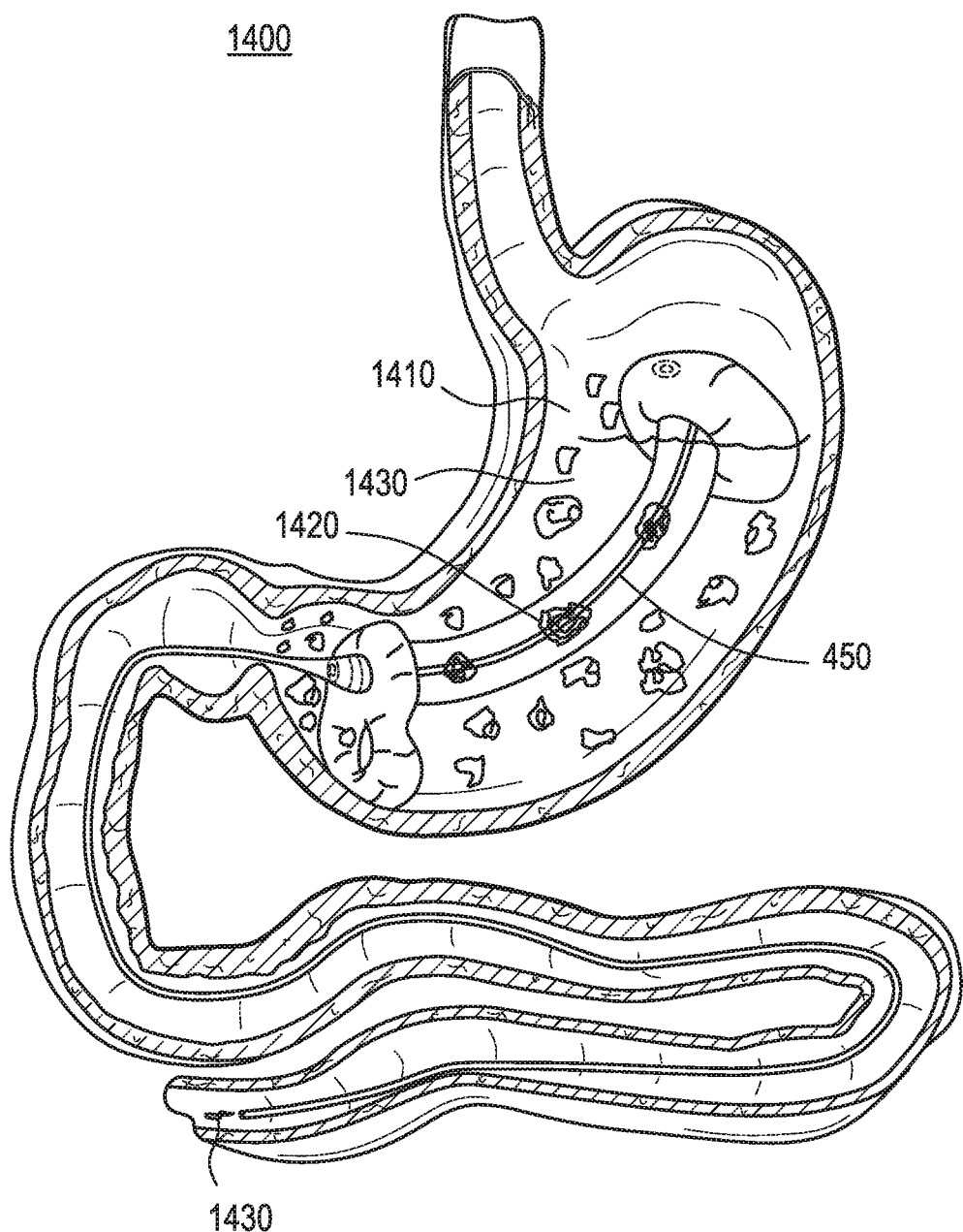
FIG. 14 illustrates chyme within the stomach surrounding the "inflatable catheter" style passive collection device.

Referring to FIG. 14, the chyme 1410 within the stomach is illustrated and consists of liquid 1430 and solid particulate components 1420. It can be seen that the particulate materials cannot pass into the open channel formed by the gaps 450 and that the central collection element 260 provides a separative functionality. It is therefore possible to provide the separation of the high calorie liquid materials 1430 from the chyme and to pass it beyond the duodenum passively. Additionally, since the central collection element 260 is produced with channels as opposed to specific lateral ports, such as those found in a typical fenestrated tube that are round or oval of other suitable shapes, there is a reduced opportunity for the device to clog, however, it may be determined that the use of a lateral port style drain type configuration may be desirable.

Figure 15:
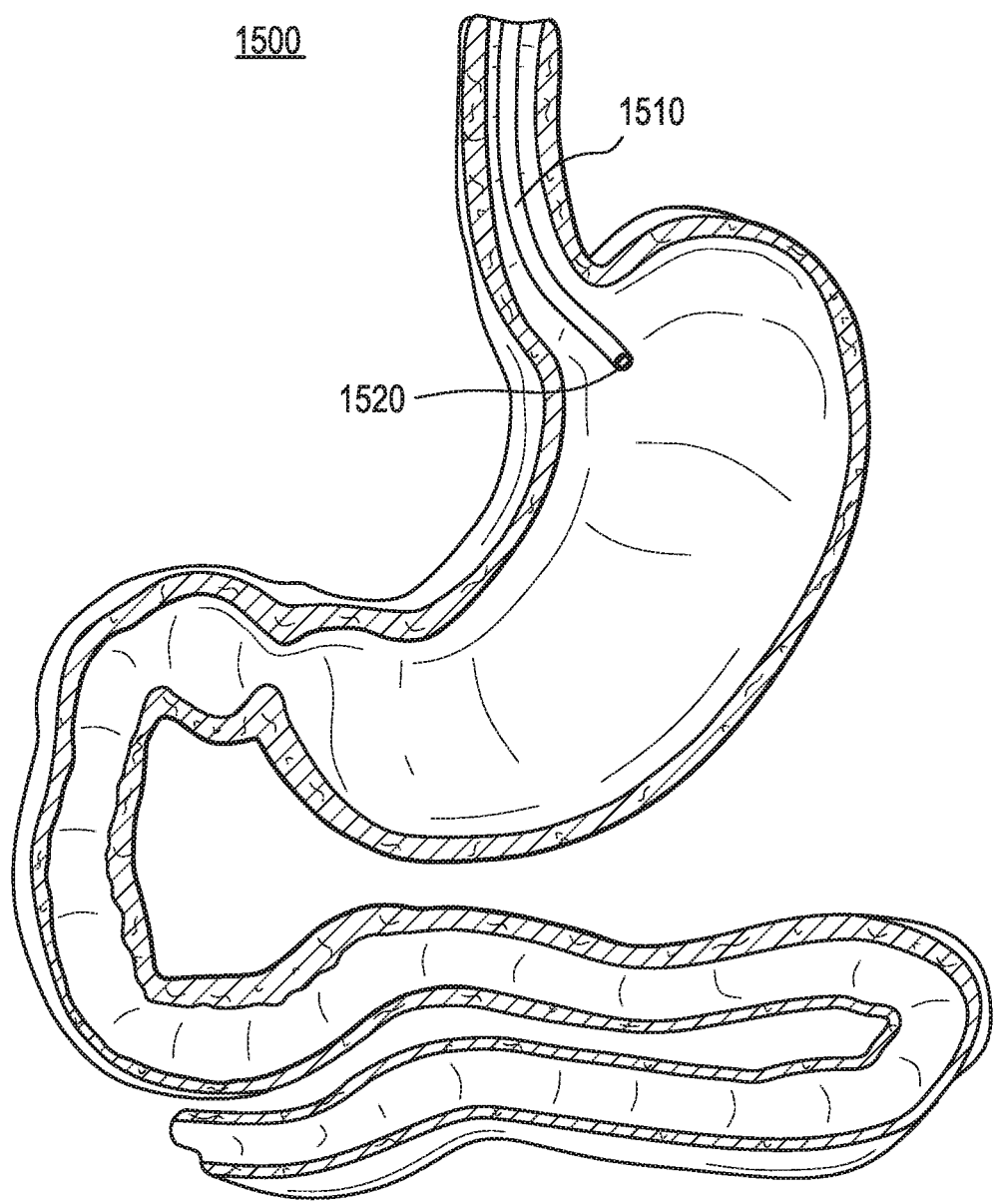
FIG. 15 illustrates an alternative embodiment of a bypass device of the present invention that is delivered through a traditional catheter approach; the collection device is compacted prior to introduction into the catheter.

Referring to FIG. 15, an alternative delivery method for the partially "inflatable catheter" style passive collection device 200 that is delivered through a traditional catheter approach is presented. A catheter 1510 is advanced through the oral cavity, through the lower esophageal sphincter. The compacted "inflatable catheter" style passive collection device 200 is packed within the distal end of the catheter 1520.

Figure 16:
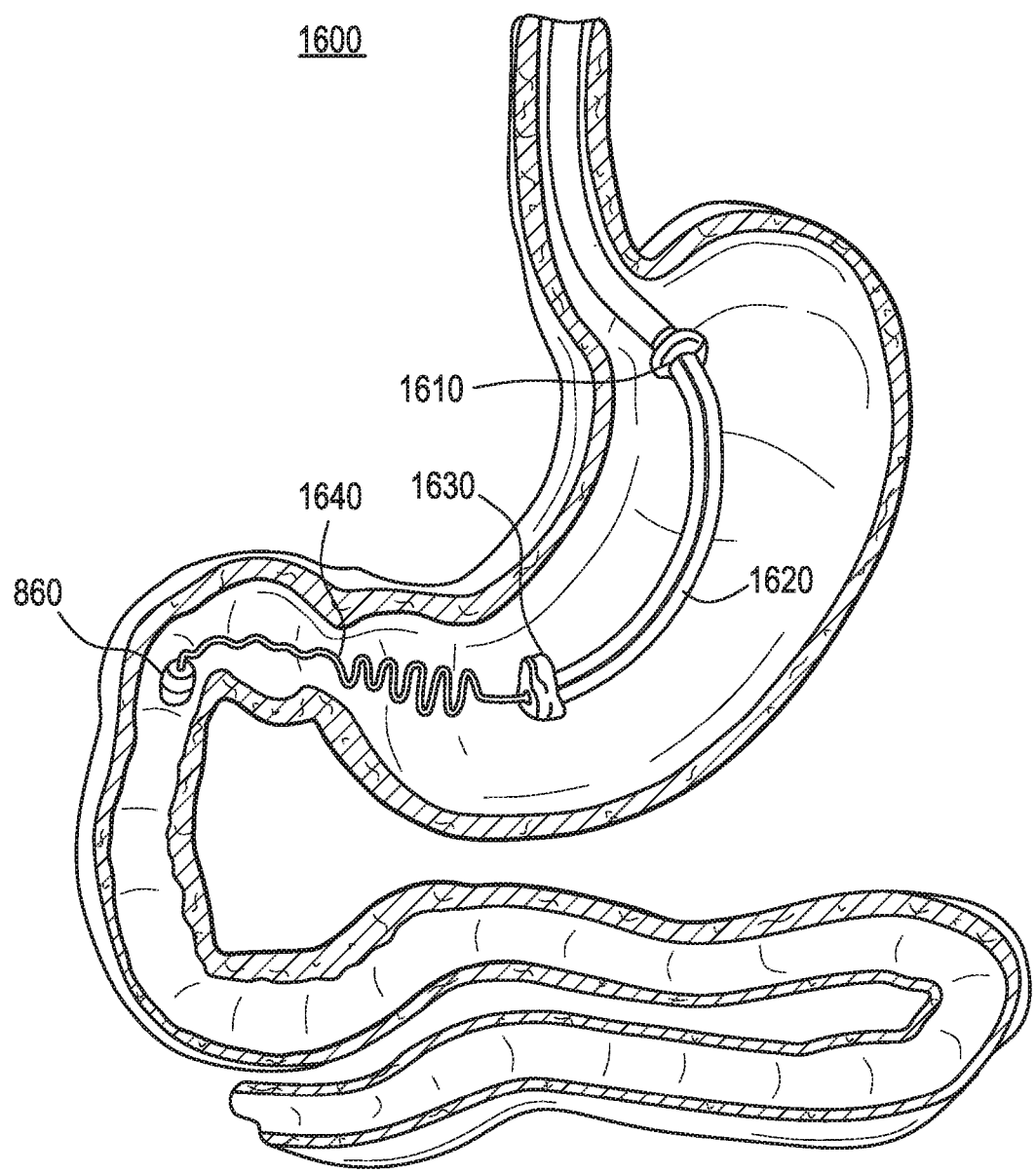
FIG. 16 shows the device of FIG. 15 after the sheath of the catheter is withdrawn.

Referring next to FIG. 16, the pusher (not shown) that is in the proximal end of the delivery catheter 1510 is held stationary and the sheath of the catheter is withdrawn over the compacted collection element. Similar to the previously-described system, the distal end of the distal transport tube is produced with a slow dissolving component 860 to facilitate passage of the distal transport tube 210 through the pylorus and into the intestines. Similar to the previously-described system, the collection unit includes two expansion elements 1630 and 1610. Unlike the previous form of the device that included the use of an inflatable central collection element 260, the device is produced with a solid central collection element 1620. The solid central collection element 1620 is extruded or molded from a conventional, biocompatible, solid polymeric or elastomeric material, such as silicone, that has been produced with the desired cruciform shape, similar to a Blake drain offered by Ethicon, Inc. Somerville, N.J. with additional fluid transmission channels.

Figure 17:
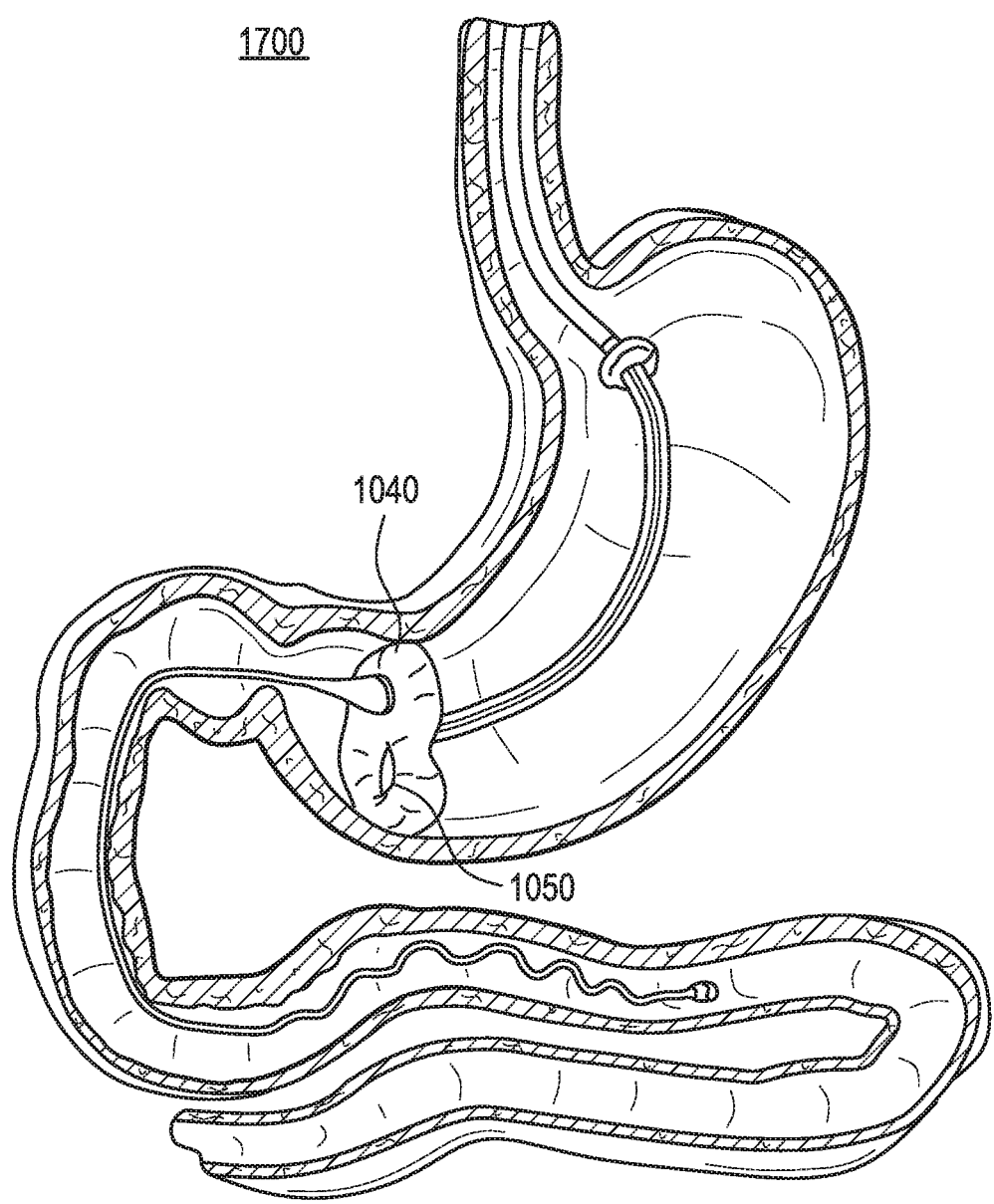
FIG. 17 shows the device of FIG. 16 with the distal expansion member expanded and with the distal transport member in the small intestine.

Referring to FIG. 17, the fluid delivery element 270 has been pressurized and the fluid causes the shift in the piston assembly thereby enabling the fluid to pass along the fluid transmission channel and into the distal expansion element 240. Similar to the previously-described fully inflatable system, the distal expansion element 240 is filled with sterile water and loses buoyancy, sinking towards the pylorus. The delivery catheter 1510 is illustrated as remaining in position within the fundus of the stomach, however, it may be desirable to withdraw the entire catheter leaving only the fluid transport element 270 in place during the inflation operations.

Figure 18:
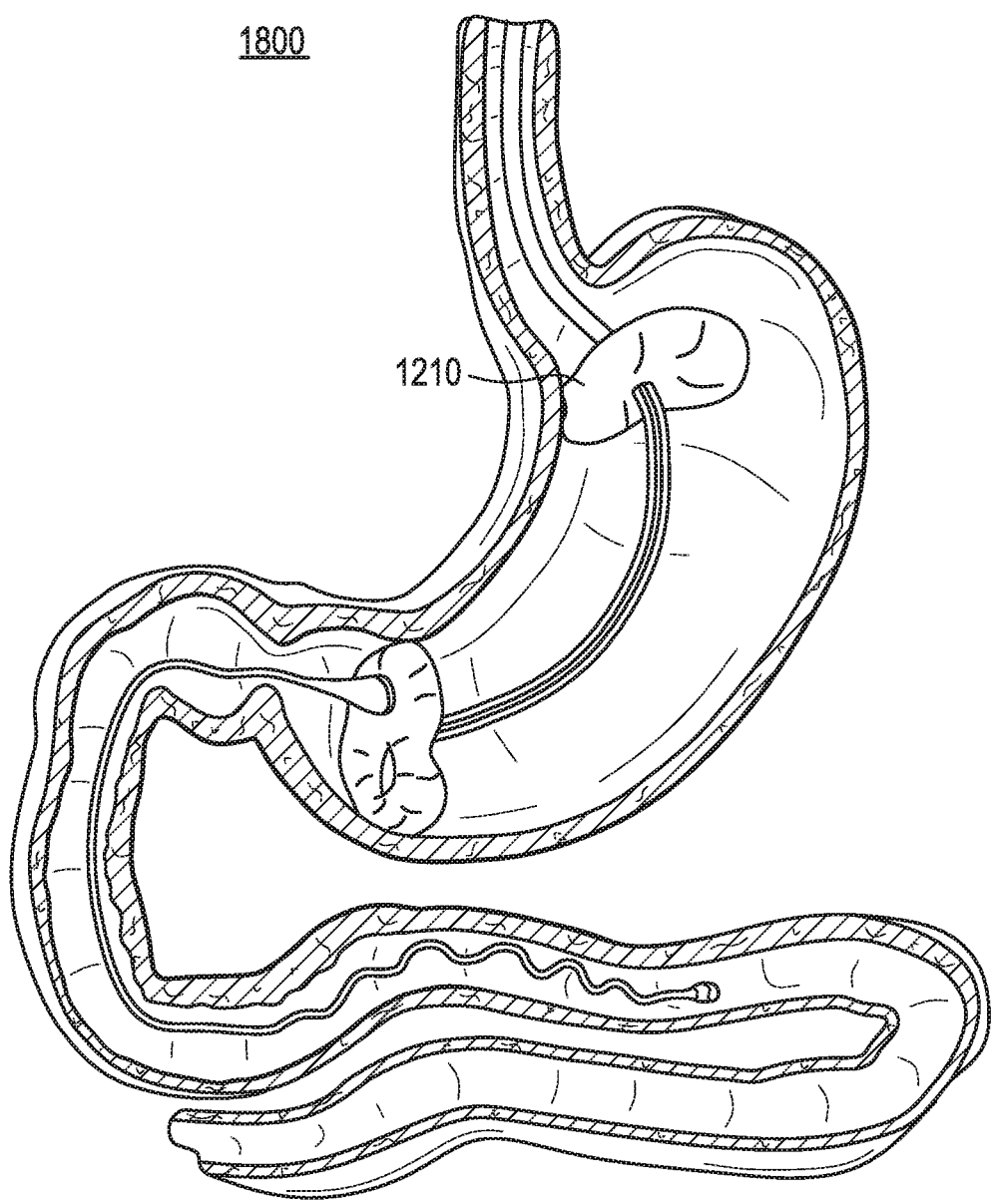
FIG. 18 shows the device of FIG. 17 with the proximal expansion member also expanded.

Referring to FIG. 18, the fluid pressurization of the distal expansion element 240 has been completed, and the proximal expansion element 250 is filled with gas as previously described.

Figure 19:
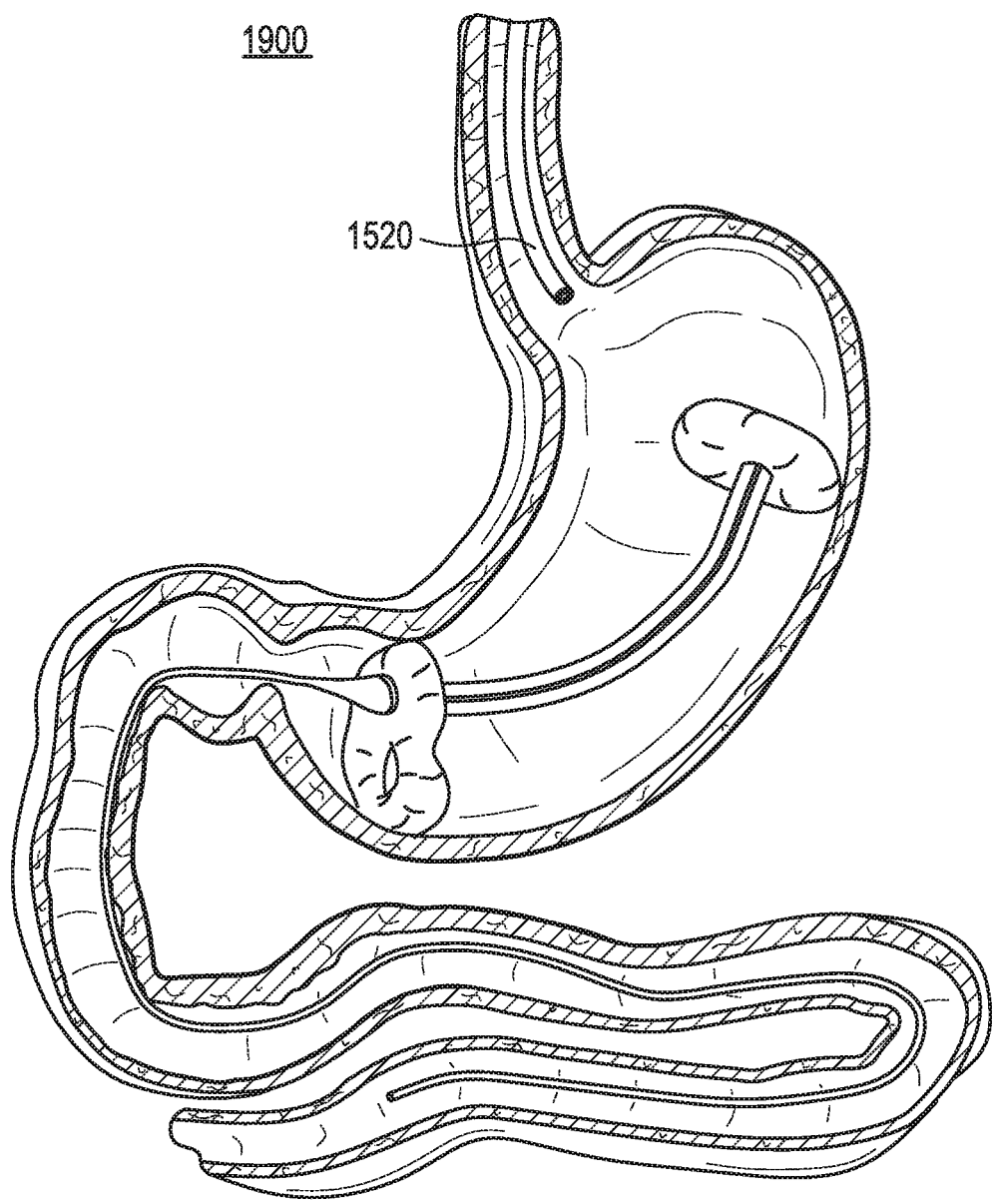
FIG. 19 shows the device of FIG. 18 released from the inflation source.

Referring to FIG. 19, the partially "inflatable catheter" style passive collection device 200 is released from the inflation source and remains in the deposited location, however, as the proximal expansion element 250 is buoyant, it remains in at least sporadic contact with the fundus, similar to the first embodiment. This buoyancy can help initiate a feeling of satiety as the upper expansion element 250 contacts the fundus signaling that the stomach is full.

Figure 20:
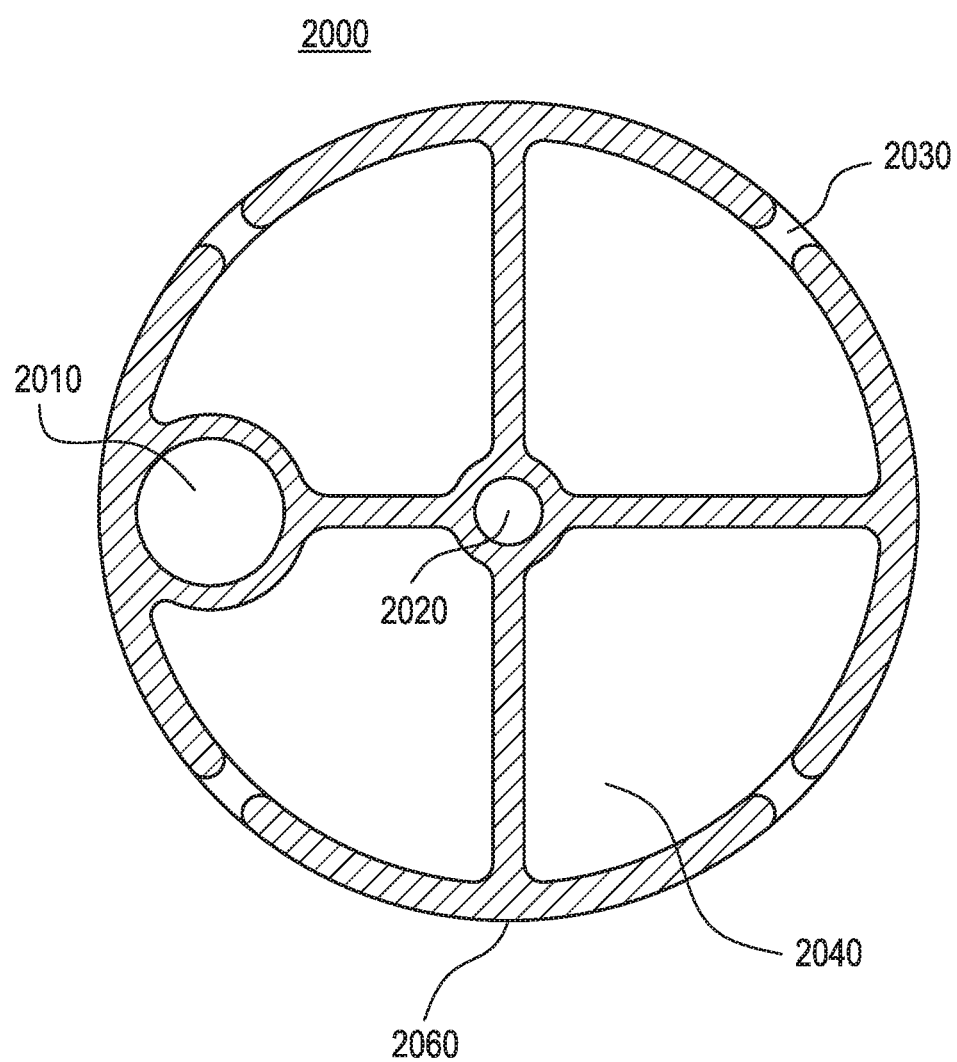
FIG. 20 is a cross-sectional view of a solid extruded collection element of the present invention.

Referring to FIG. 20, the cross-sectional view of the solid extruded form of the central collection element 1620 described in the second embodiment, of the partially "inflatable catheter" style passive collection device 200, is illustrated. The cross-sectional form remains as a basic cruciform as previously described for "inflatable catheter" style passive collection device 200, however, other shapes such as bisected ovals, circles, rectangles triangular forms, etc. may be considered as suitable as well. The outer portions of the circular perimeter wall 260 are interrupted by gaps 2030 as previously detailed to form channels along the length of the collection element. Inner channels 2040 for carrying fluid are created by the extruded form. In order to provide a pathway for fluid to travel for inflating the distal expansion element 240, a cylindrical channel 2010 has been formed near the outer perimeter of the form. In this position, the side wall of the extruded form can be ported to enable fluid connection with the inner volume of the distal expansion element 240. The proximal end of central collection element 1620 is mated to an eccentrically located engagement element, not shown, to provide similar functionality to the first embodiment disclosed. The form may be produced with a central lumen 2020 if so desired or the cross-section of the intersecting webs may be solid in form. The cross-sectional shape may transform into a fully cylindrical extruded form at the distal end, similar to a standard Blake style surgical drain.

Figure 21:
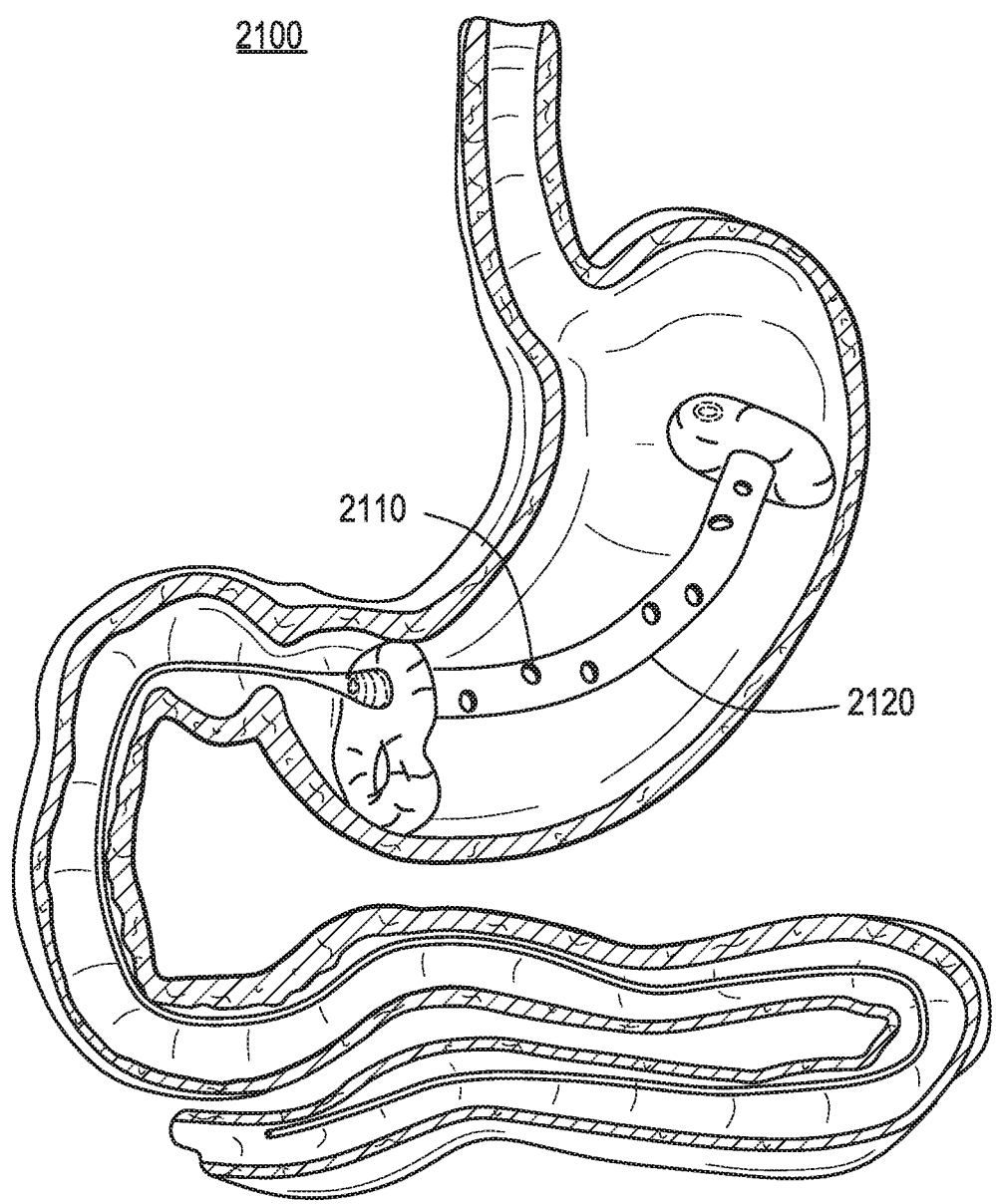
FIG. 21 is an illustration of a fenestrated collection element of the present invention.

Referring to FIG. 21, a fenestrated central collection element 1620 is illustrated as an additional alternative embodiment. The cylindrical wall 2120 is produced with a cylindrical channel 2010 similar to the one in illustrated in FIG. 20. Randomly or uniformly spaced fenestrations 2110 are punched into the side wall 2120 of the central collection element 1620 and allow fluid, and some small particulate of ingested matter to enter the inner volume of the central collection element 1620 and to be transported distally past the duodenum.

Figure 22:
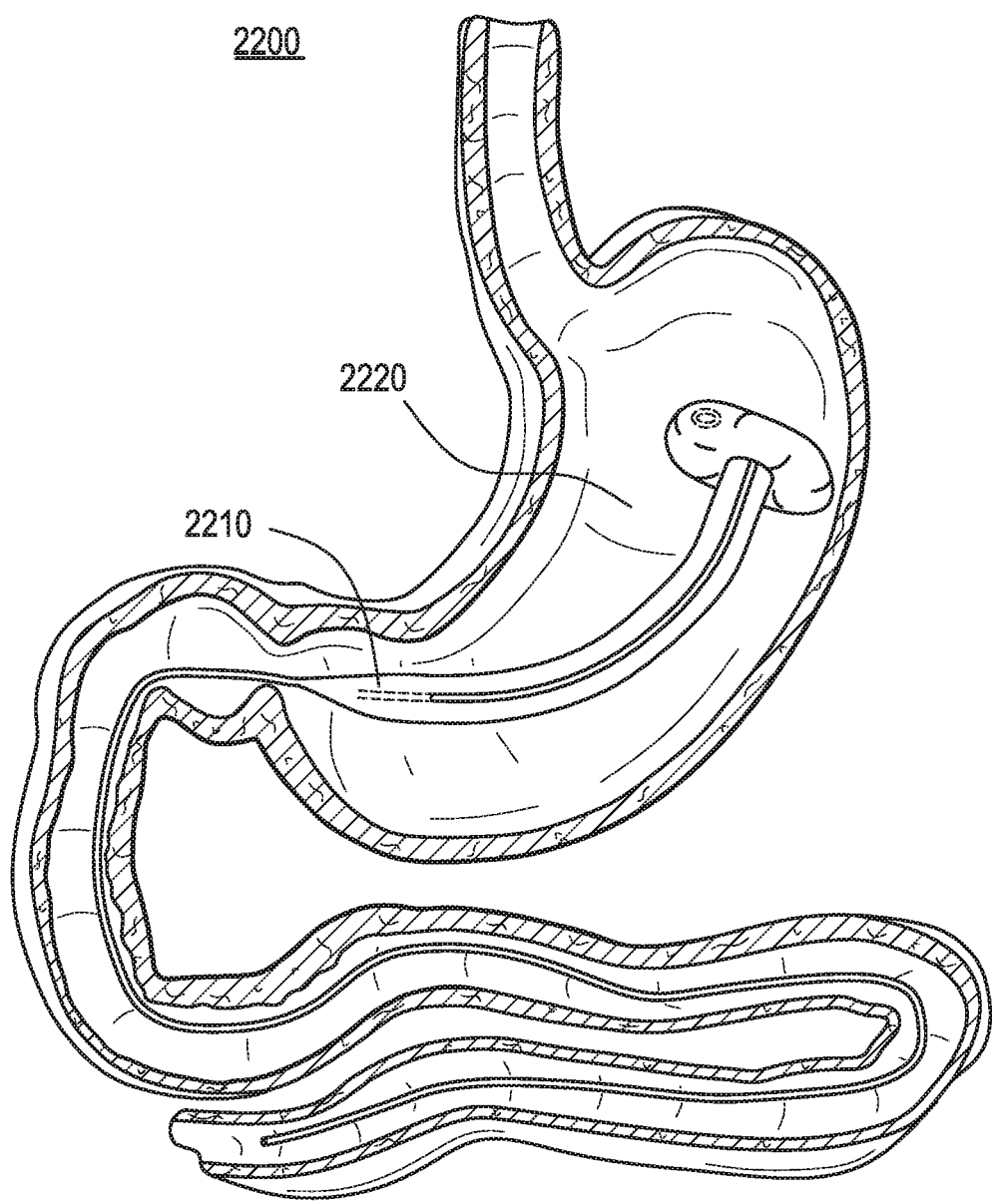
FIG. 22 is an alternate embodiment of a bypass device of the present invention having a buoyancy expansion element on the proximal end of the collection element.

Referring to FIG. 22, an alternate form of the device 2200 that only utilizes a buoyancy proximal expansion element 250 on the proximal end is illustrated. The proximal end has the inflatable proximal expansion element 250 that is filled with gas as previously described, while the balance of the collection element 2220 and the distal fluid transport element may move within the chyme and assume some position depending upon the density of the surrounding chyme versus the density of the material selected for the formation of the collection element 2220. Further, the transitional location of the collection element 2220 with the cruciform shape into the fully hollow cylindrical cross-sectional form is identified as 2210.

Figure 23:
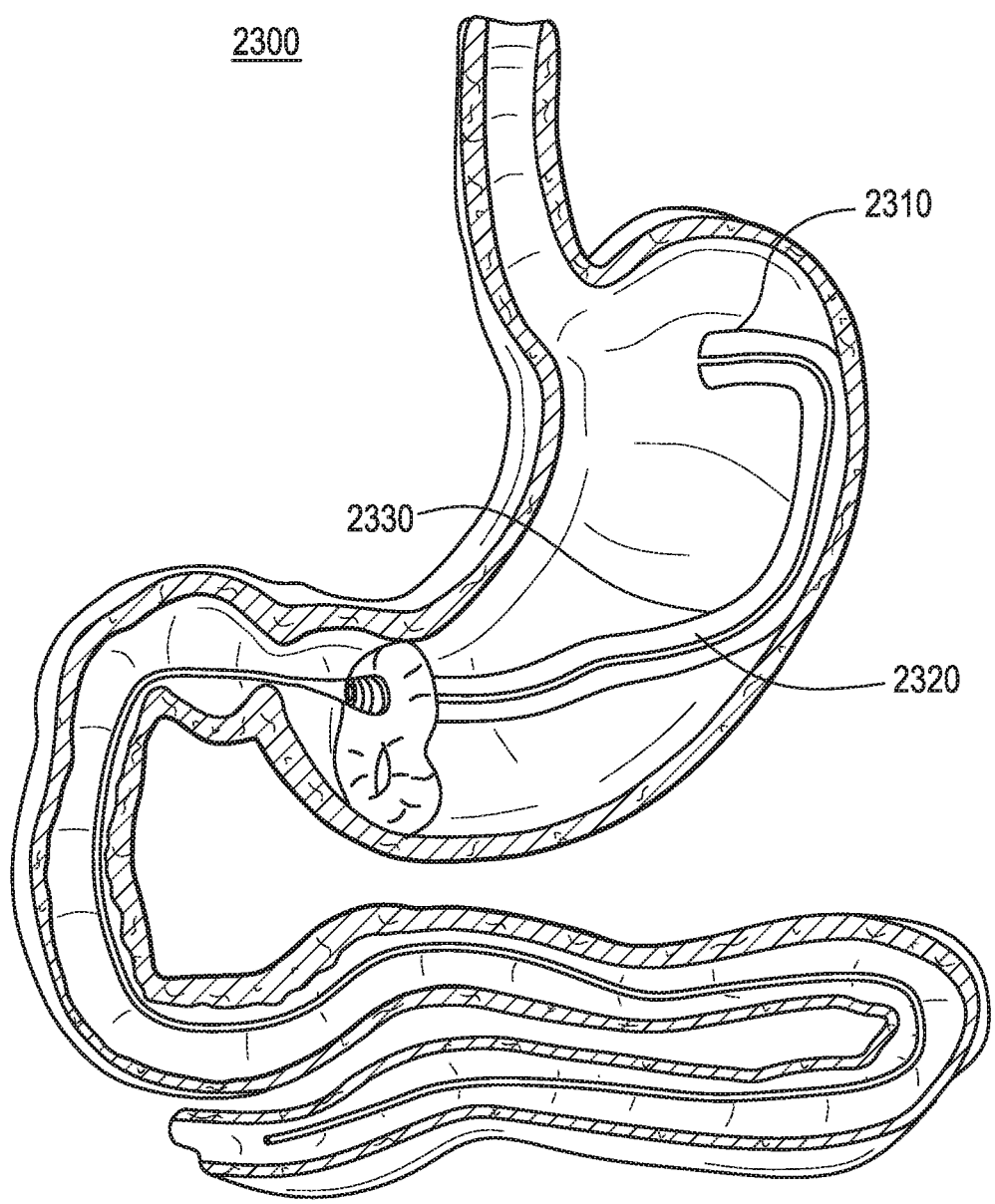
FIG. 23 is an alternate embodiment of a bypass device of the present invention having a distal expansion element on the distal end of the collection element.

Referring to FIG. 23, an embodiment of the passive caloric bypass device of the present invention that relies upon the inflation of a distal expansion element 240 with fluid 2300 is illustrated. In this particular embodiment, the device 2300 is produced with the previously described distal inflation element 240, however, the distal expansion element 240 may be produced with an engagement port directly in the wall of the distal expansion element 240 for direct connection to the fluid transport element 270. The proximal end of the device 2300 is open, similar to the traditional Blake style surgical drain. It may be advantageous to produce the central collection element 2330 with a curvature that is small in radius 2320 rather than the natural radius of the stomach fundus to prevent erosion due to contact of the free end of the collection element with the stomach lining.

Figure 24:
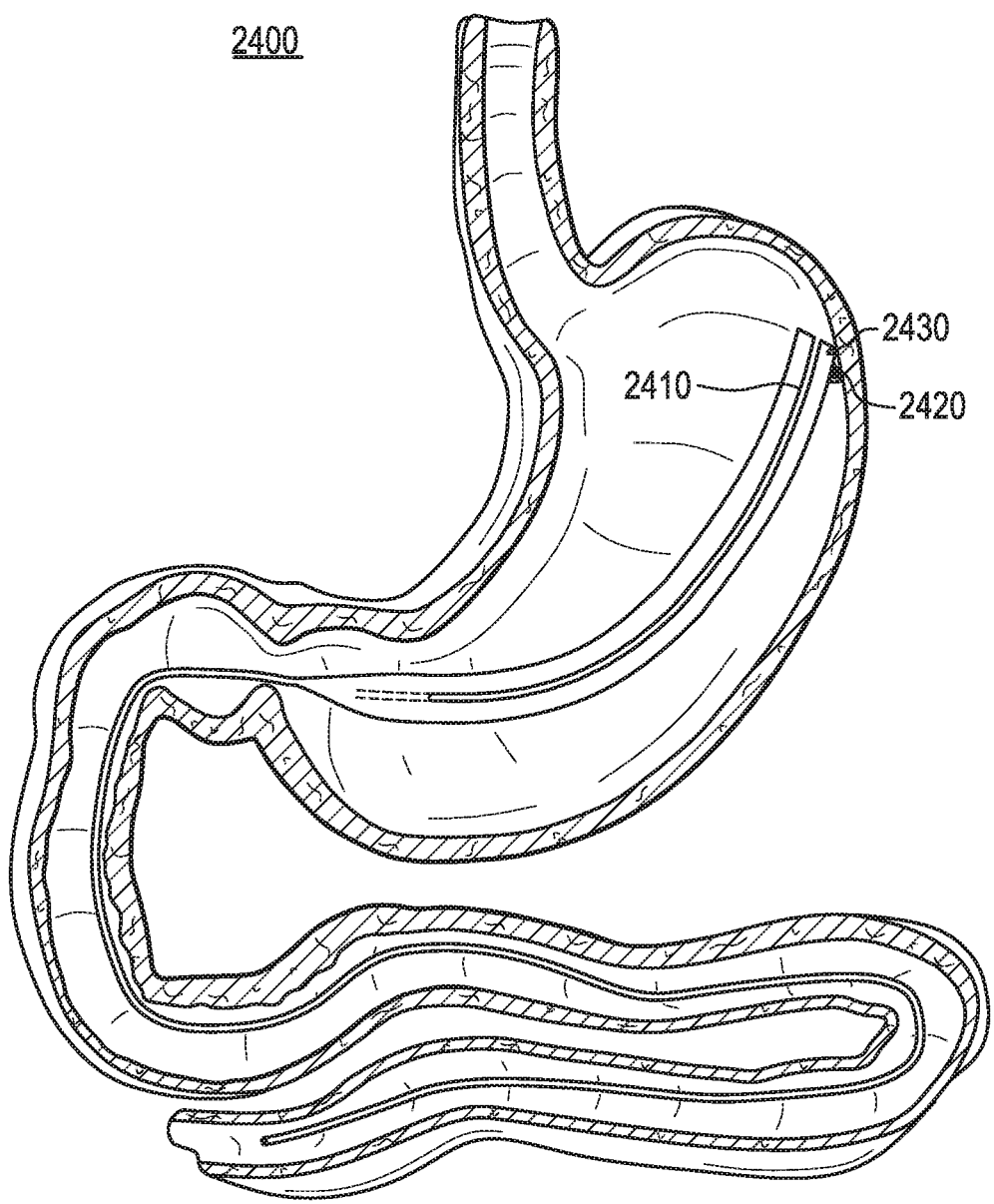
FIG. 24 is an alternate embodiment of a bypass device of the present invention without expansion elements; the proximal end of the collection element is secured to a location on the stomach wall.

Referring to FIG. 24, an embodiment of the passive bypass device of the present invention that is similar to a traditional Blake style surgical drain is disclosed. In this embodiment, device 2400 is placed within the stomach through the catheter approach previously described, however, the proximal end of the collection element 2410 may be fastened to the wall of the stomach through the use of a conventional surgical fastening element 2420, illustrated as a suture-type attachment, that passes through a receiving feature 2430 in the collection element side wall. The receiving feature 2430 may be pre-formed as a hole or lug or other feature or may be created through the piercing of the wall of the collection element with a needle or staple or other such sharp device.

It will be appreciated the maximum cross-sectional size of the collection element, whether inflatable or not, frequently and preferably will be greater than the maximum cross-sectional size of the distal transport member. In addition, the maximum cross-sectional size of the distal transport member will be such as to effectively pass through the pylorus while maintaining a sufficient amount of space between the outer surface of the distal transport member and the inner wall of the pylorus to effectively allow chime, liquids, and food particles to pass through the Pyloric valve 160.

It should be noted that features such as absorbability of various components during the course of the device life may be desirable. An example of this would be the use of a bioabsorbable or biodegradable material for the distal fluid transport element 210. The use of the bioabsorbable or biodegradable material would result in the reduction and final release of the distal transport element within the intestines and subsequent passage of the element from within the GI tract. In this form, retrieval of the upper portions of the collection element would not involve the potential binding of the distal transport element within the distal intestines in the serpentine pattern that would exist. This feature would also serve to enable greater lengths of the distal fluid transport element to further minimize the opportunity of caloric absorption and potentially decrease the timing of negative feedback to the patient on poor eating habits. Examples of biodegradable or bioabsorbable materials include but are not limited to conventional biocompatible materials including polyester polymers such as polylactic acid, polyglyclolide, epsilon-caprolactone, polylactide, and the like and copolymers thereof. The non-absorbable polymers used to construct the passive caloric bypass devices of the present invention include biocompatible conventional materials such as polyamides and engineered nylons such as Pebax®, Grilamid®, and Vestamid®, polyethylene terephthalate (PET), polyurethanes, polyethylene, polyolefins, silicone and or natural rubber.

Beyond these embodiments, it may be determined that it is preferable to produce a collection element that limits the fluids and materials that are to be bypassed. If the channels or fenestrated regions are limited to the proximal portion of the collection element, chyme that does not reach that elevation within the stomach will be unaffected. This may limit the passage of too much acid to locations distal to the duodenum thereby minimizing negative long-term consequences.

Additionally, it may be desirable to incorporate anti-microbial agents either on or in the device. The anti-microbial agents may be included directly in the extruded materials or may be coated onto the device through the use of secondary processing. Further, it may be desirable to include anti-microbial agents only in portions of the device, such as the distal transport tube, to prevent bacterial colonization of the device or in an attempt to affect the local microbiome. Agents including oligodynamic metals such as silver, Triclosan, Iodine iodized compounds, Chlorhexadine Gluconate, antibiotics and chemotherapeutic drugs or other known anti-microbial agents may be utilized.

While various embodiments of the subject invention are disclosed, each embodiment provides the means for the extraction of fluid with solubilized sugars and dispersed starches to enter within a free space of a device and to be transported away from the primary location of absorption. Additionally, the transportation of a significant portion of the sugars and starches away from the site of absorption emulates two aspects of the duodenal switch surgeries. One aspect is that the sugars are not absorbed and the second aspect is that the deposition of sugars directly into the ileum provides a biological feedback stimulus to the patient. This biofeedback, in the form of dumping syndrome, helps to teach the patient to avoid foods that are high in sugar and simple starches and thereby drives a behavioral change. Additionally, since the device is temporary in nature, and is delivered through an upper GI endoscopic approach, it may be retrieved as necessary or after patient behavior has been acceptably modified.

Although this invention has been shown and described with respect to detailed embodiments thereof, it will be understood by those skilled in the art that various changes in form and detail thereof may be made without departing from the spirit and scope of the claimed invention.

I claim:

1. A passive caloric bypass device, comprising:
   an inflatable separative collection element having a structure with a proximal end and a distal end, the structure having at least one longitudinal fluid channel and at least one fluid entry opening in communication with each fluid channel, and wherein the structure has a hollow interior chamber for receiving an inflation fluid to place the structure into an expanded state;
   a distal transport member having a proximal end and a distal end in fluid communication with the collection element, wherein the proximal end of the transport element is mounted to the distal end of the collection element;
   a proximal expansion member mounted to the proximal end of the collection element; and
   a distal expansion element mounted to the distal end of the collection element,
   wherein the proximal expansion member and the distal expansion member are each capable of selectively receiving an inflation medium via a single input port to selectively expand one or another, or both, of said proximal end distal expansion members, and wherein said inflation medium for said distal expansion member is a fluid and said inflation medium for said proximal expansion member is a gas,
   wherein the device additionally comprises a valve assembly for selectively directing said fluid inflation medium to the distal expansion member and said gas inflation medium to the proximal expansion member.

2. The device of claim 1, wherein said valve assembly includes said an input port, and wherein said input port is capable of connection to said fluid or gas inflation medium.

3. A passive caloric bypass device, comprising:
   an inflatable separative collection element having a structure with a proximal end and a distal end, the structure having at least one longitudinal fluid channel and at least one fluid entry opening in communication with each fluid channel, and wherein the structure has a hollow interior chamber for receiving an inflation fluid to place the structure into an expanded state;
   a distal transport member having a proximal end and a distal end in fluid communication with the collection element, wherein the proximal end of the transport element is mounted to the distal end of the collection element;
   a proximal expansion member mounted to the proximal end of the collection element; and
   a distal expansion element mounted to the distal end of the collection element,
   wherein the proximal expansion member and the distal expansion member are each capable of selectively receiving an inflation medium via a single input port to selectively expand one or another, or both, of said proximal end distal expansion members, and wherein said inflation medium for said distal expansion member is a fluid and said inflation medium for said proximal expansion member is a gas, and wherein the structure has a cruciform cross-section comprising at least two extension elements extending outwardly from a central element, the extension elements having a proximal end adjacent to the central element and a distal end, and a perimeter segment mounted to the distal end of each extension element, the perimeter segments separated from each other by gaps.

4. The device of claim 3, wherein the perimeter segments are curved and the cross-section has a circular form.

5. The device of claim 3, wherein the central element additionally comprises a central lumen.

6. A passive caloric bypass device, comprising:

a separative collection element having a structure with a proximal end and a distal end, a proximal expansion member mounted to the proximal end of the collection element, and a distal expansion member mounted to the distal end of the collection element, the structure having at least one longitudinal fluid channel and at least one fluid entry opening in communication with each fluid channel; and, a distal transport member having a proximal end and a distal end in fluid communication with the collection element, wherein the proximal end of the transport element is mounted to the distal end of the collection element, wherein the proximal expansion member and the distal expansion member are each capable of selectively receiving an inflation medium via a single input port to selectively expand one or another, or both, of said proximal end distal expansion members, and wherein said inflation medium for said distal expansion member is a fluid and said inflation medium for said proximal expansion member is a gas, and wherein the structure has a cruciform cross-section comprising at least two extension elements extending outwardly from a central element, the extension elements having a proximal end adjacent to the central element and a distal end, and a perimeter segment mounted to the distal end of each extension element, the perimeter segments separated from each other by gaps.

7. The device of claim 6, wherein the perimeter segments are curved and the cross-section has a circular form.

8. A passive caloric bypass device, comprising:

a separative collection element having a structure with a proximal end and a distal end, the structure having at least one longitudinal fluid channel and at least one fluid entry opening in communication with each fluid channel; and, a distal transport member having a proximal end and a distal end in fluid communication with the collection element, wherein the proximal end of the transport element is mounted to the distal end of the collection element, wherein the structure has a cruciform cross-section comprising at least two extension elements extending outwardly from a central element, the extension elements having a proximal end adjacent to the central element and a distal end, and a perimeter segment mounted to the distal end of each extension element, the perimeter segments separated from each other by gaps.

9. The device of claim 8, wherein the collection element is inflatable and the structure comprises a hollow interior chamber for receiving an inflation medium to place the structure in an expanded state.

* * * * *